United States Patent
Yoshitomo et al.

(10) Patent No.: US 7,586,009 B2
(45) Date of Patent: Sep. 8, 2009

(54) BIS-(HYDROXYBENZALDEHYDE) COMPOUND AND NOVEL POLYNUCLEAR POLYPHENOL COMPOUND DERIVED THEREFROM AND METHOD FOR PRODUCTION THEREOF

(75) Inventors: Akira Yoshitomo, Wakayama (JP); Tatsuya Iwai, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 68 days.

(21) Appl. No.: 11/817,113

(22) PCT Filed: Feb. 23, 2006

(86) PCT No.: PCT/JP2006/303222

§ 371 (c)(1),
(2), (4) Date: Sep. 21, 2007

(87) PCT Pub. No.: WO2006/090757

PCT Pub. Date: Aug. 31, 2006

(65) Prior Publication Data

US 2009/0076310 A1    Mar. 19, 2009

(30) Foreign Application Priority Data

Feb. 25, 2005 (JP) .............................. 2005-050787
Feb. 25, 2005 (JP) .............................. 2005-050796
Dec. 21, 2005 (JP) .............................. 2005-368205

(51) Int. Cl.
*C07C 45/00* (2006.01)
*C07C 47/57* (2006.01)
*C07C 39/15* (2006.01)

(52) U.S. Cl. .................. 568/433; 568/442; 568/720

(58) Field of Classification Search ................ 568/433, 568/442, 720
See application file for complete search history.

(56) References Cited

FOREIGN PATENT DOCUMENTS

| JP | 11-199533 | 7/1999 |
| JP | 2000-1448 | 1/2000 |
| JP | 2001-312055 | 11/2001 |

OTHER PUBLICATIONS

Ali Khalafi-Nezhad, et al., "Synthesis of Polyfunctional Aromatic Ring Systems (Phloroglucide Analogs) under Microwave Irradiation," Helvetica Chemica Acta—vol. 86 (2003) pp. 2396-2403.

*Primary Examiner*—Sikarl A Witherspoon
(74) *Attorney, Agent, or Firm*—Knobbe, Martens, Olson & Bear LLP

(57) ABSTRACT

Provide a new bis-(hydroxybenzaldehyde) compound, as well as a new polynuclear polyphenol compound derived therefrom, suitable for use as component materials for photosensitive resist compositions, component materials and hardeners for epoxy resins, developers and anti-fading agents used in thermosensitive recording materials, bactericides, fungicides, antioxidants and other functional chemical products or component materials thereof, wherein such bis-(hydroxybenzaldehyde) compound is produced by reacting in the presence of trihalogenated acetic acid catalyst or phosphoric acid catalyst a 2,6-di(hydroxymethyl)-4-alkylphenol with a hydroxybenzaldehyde expressed by general formula (14).

17 Claims, No Drawings

BIS-(HYDROXYBENZALDEHYDE) COMPOUND AND NOVEL POLYNUCLEAR POLYPHENOL COMPOUND DERIVED THEREFROM AND METHOD FOR PRODUCTION THEREOF

BACKGROUND OF THE INVENTION

1. Technical Field

The present invention relates to a new bis-(hydroxybenzaldehyde) compound and a new polynuclear polyphenol compound derived therefrom, and specifically to a bis-(hydroxybenzaldehyde) compound (also referred to as bis-(formyl phenol) compound) having a formyl hydroxyphenyl group, via a methylene group, in the ortho position with respect to the hydroxyl group in the hydroxyphenyl nucleus at the center of the molecule, as well as a polynuclear polyphenol compound comprising the aforementioned compound with a phenol further bonded to the formyl groups at both ends.

More specifically, the present invention relates to a 2,6-bis-[(formyl hydroxyphenyl)methyl]-4-alkyl phenol compound having two formyl hydroxyphenyl groups mutually bonded, via a methylene group, to a p-alkyl substituted phenol; or a bis-(hydroxybenzaldehyde) compound having two hydroxybenzaldehyde groups mutually bonded, via a methylene group, to a polyphenol skeleton, where a cyclohexyl substituted group with excellent lipophilic property is included in the two phenol nucleuses of cyclohexyl bis-phenol; as well as a hydroxybenzil substituted polynuclear polyphenol compound derived therefrom.

These compounds are useful as component materials for photosensitive resist compositions, component materials and hardeners for epoxy resins, developers and anti-fading agents used in thermosensitive recording materials, bactericides, fungicides, antioxidants and other functional chemical products or component materials thereof.

2. Prior Art

Traditionally, bis-phenol compounds have been used widely as component materials for photosensitive resists, component materials and hardeners for epoxy resins, component materials for phenol resins, developers and anti-fading agents used in thermosensitive recording materials, bactericides, fungicides, and antioxidants, among others, as well as component materials thereof.

In recent years, demand for finer processing is requiring improvements in various performance properties such as higher sensitivity, higher resolution and greater development property for photosensitive resin materials, among others, in certain fields such as electronic components. In these fields, a number of new bis-phenol compounds have been proposed to address the demand for resist resins offering higher performance and function. For example, derivatives having a polynuclear aromatic compound as their skeleton are drawing the attention in the area of electron beam lithography, etc.

Among these bis-phenol compounds, of particular interest are bis-(hydroxybenzaldehyde) compounds obtained by using, as one component material, a 2,6-dimethylol-4-alkyl phenol obtained by reacting a p-alkyl phenol with a formaldehyde, and then reacting the material with various formyl substituted phenol compounds, because such bis-(hydroxybenzaldehyde) compounds have three aromatic nucleuses, possess a symmetrical molecular structure around the p-alkyl phenol nucleus at the center of the molecule, and also have functional groups including one hydroxyl group in the p-alkyl phenol nucleus at the center of the molecule and two phenolic hydroxyl groups and formyl groups at the ends of the molecule. These bis-phenol compounds are expected to offer improved levels of various reactivities and solubility in organic solvents, and therefore using them as component materials will likely create materials exhibiting improved heat resistance, water resistance, moisture absorption resistance and lower dielectric constant, among others.

Several bis-(formylphenol) compounds having such symmetrical structure are already known.

For example, Helvetica Chimica Acta (2003), 86 (7), 2396-2403 discloses 2,6-di(5-formyl-2-hydroxyphenyl)methyl-4-chlorophenol synthesized from a substituted phenol and 2,6-dihydroxy methyl-4-chlorophenol under irradiation of electron beam using zinc chloride as a catalyst or in a methanol solvent using hydrochloric acid as a catalyst. Another example is Japanese Patent Laid-open No. 2000-1448 that describes hydroxymethyl substituted 1,1-bis-cyclohexane, which is used as a component material for the bis-(hydroxybenzaldehyde) compound proposed by the present invention.

Also, Japanese Patent Laid-open No. Hei 11-199533 describes polynuclear polyphenol compound constituted by trisphenol skeletons of trisphenol methane type mutually bonded via a methylene group.

Patent Literature 1: Japanese Patent Laid-open No. 2000-1448

Patent Literature 2: Japanese Patent Laid-open No. Hei 11-199533

Non-patent Literature 1: Helvetica Chimica Acta (2003), 86 (7), 2396-2403

SUMMARY OF THE INVENTION

Problems to be Solved by the Invention

Accordingly, the object of the present invention is to provide a new bis-(hydroxybenzaldehyde) compound suitable for use as component materials for various functional materials or component materials for photo resists for semiconductors, etc., and a method for producing the same, as well as a new polynuclear polyphenol compound derived therefrom.

Means for Solving the Problems

The new bis-(hydroxybenzaldehyde) compound proposed by the present invention is expressed by general formula (1) given below.

[Chemical Formula 1]

A bis-(hydroxybenzaldehyde) compound expressed by

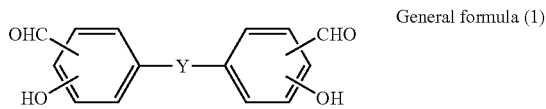

General formula (1)

(wherein Y represents a bivalent group having a methylene group at both ends, as expressed by general formula (2) or general formula (3) given below)

[Chemical Formula 2]

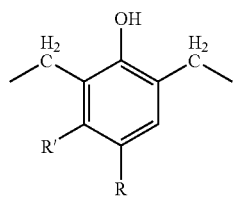

General formula (2)

(wherein R represents an alkyl group with 1 to 4 carbon atoms or cycloalkyl group with 5 or 6 carbon atoms, while R' represents a hydrogen atom or methyl group)

[Chemical Formula 3]

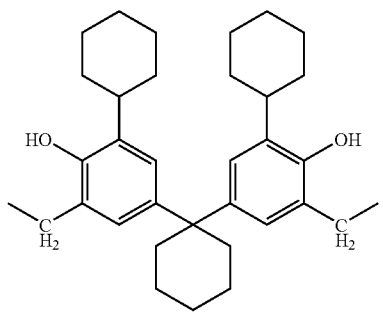

General formula (3)

To be specific, the bis-(hydroxybenzaldehyde) compound proposed by the present invention is expressed by general formula (4) or general formula (7) given below.

[Chemical Formula 4]

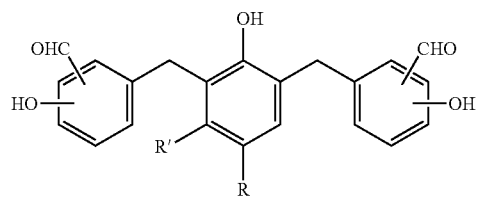

General formula (4)

(wherein R and R' represent the corresponding items in general formula (2), respectively)

[Chemical Formula 5]

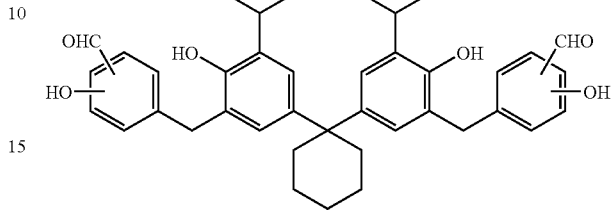

General formula (7)

This bis-(hydroxybenzaldehyde) compound can be produced by, for example, reacting in the presence of an acid catalyst a 2,6-di(hydroxymethyl)-4-alkylphenol expressed by general formula (12), or a 1,1-bis-(3-cyclohexyl-4-hydroxy-5-hydroxymethyl phenyl)cyclohexane expressed by general formula (13), with a hydroxybenzaldehyde expressed by general formula (14).

[Chemical Formula 6]

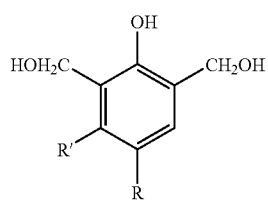

General formula (12)

(wherein R and R' represent the corresponding items in general formula (2), respectively)

[Chemical Formula 7]

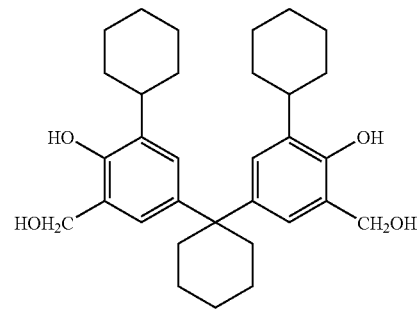

General formula (13)

[Chemical Formula 8]

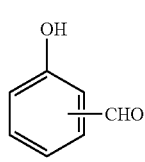

General formula (14)

Furthermore, the polynuclear polyphenol compound proposed by the present invention is expressed by general formula (8) given below.

[Chemical Formula 9]

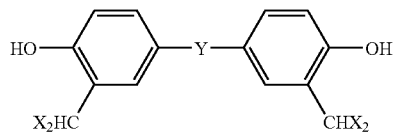

General formula (8)

(wherein Y represents the corresponding item in general formula (1), while X represents a hydroxyphenyl group that may be substituted by an alkyl group expressed by general formula (9) given below)

[Chemical Formula 10]

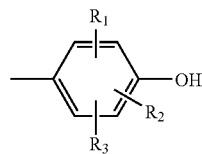

General formula (9)

(wherein $R_1$, $R_2$ and $R_3$ each represent an independent hydrogen atom, alkyl group with 1 to 4 carbon atoms, or cycloalkyl group with 5 or 6 carbon atoms)

To be specific, the polynuclear polyphenol compound proposed by the present invention is expressed by general formula (10) or general formula (11) given below.

[Chemical Formula 11]

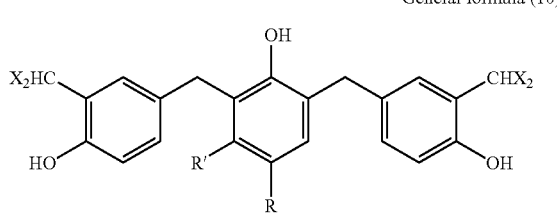

General formula (10)

(wherein R and R' represent the corresponding items in general formula (2), respectively, while X is the same as the hydroxyphenyl group in general formula (9))

[Chemical Formula 12]

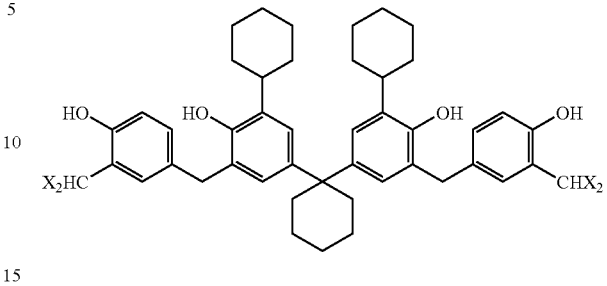

General formula (11)

(wherein X represents the corresponding item in general formula (9))

This polynuclear polyphenol compound proposed by the present invention can be produced by, for example, reacting in the presence of an acid catalyst a bis-(hydroxybenzaldehyde) compound expressed by general formula (16) given later, or a 1,1-bis-[3-(3-formyl-4-hydroxyphenyl)methyl-4-hydroxy-5-cyclohexylphenyl]cyclohexane, with a phenol expressed by general formula (15) given below.

[Chemical Formula 13]

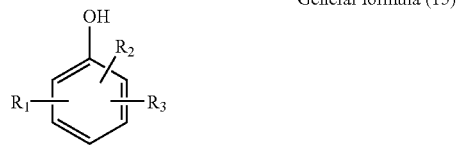

General formula (15)

(wherein $R_1$, $R_2$, and $R_3$ represent the corresponding items in general formula (9), respectively, each being an independent hydrogen atom, alkyl group with 1 to 4 carbon atoms, or cycloalkyl group with 5 or 6 carbon atoms; however, they are not substituted in position 4 with respect to the hydroxyl group)

EFFECTS OF THE INVENTION

The new bis-(hydroxybenzaldehyde) compound expressed by general formula (4) as proposed by the present invention has three aromatic nucleuses and therefore demonstrates excellent heat resistance, lipophilic property and moisture absorption resistance, among others. It also has a symmetrical molecular structure around the p-alkyl phenol nucleus at the center of the molecule, as well as three phenolic hydroxyl groups and two phenolic aldehyde groups bonded to the above aromatic nucleuses, which translates to various reactivities and makes the compound useful in a wide range of applications as an intermediate reaction material. This bisphenol compound is expected to offer improved levels of various reactivities and solubility in organic solvents, and therefore using it as a component material will likely create materials exhibiting improved heat resistance, water resistance, moisture absorption resistance and lower dielectric constant, among others.

Also, the new bis-(hydroxybenzaldehyde) compound expressed by general formula (7) as proposed by the present invention has four aromatic nucleuses and three cyclohexyl groups, and therefore offers excellent heat resistance, lipophilic property and moisture absorption resistance, among others. It also has four phenolic hydroxyl groups and two phenolic aldehyde groups bonded to the above aromatic nucleuses, which translates to various reactivities and makes the compound useful in a wider range of applications as an intermediate reaction material.

The new polynuclear polyphenol compound expressed by general formula (8), also proposed by the present invention, has two di(hydroxyphenyl)methyl-hydroxybenzil groups as substituent groups around the center skeleton consisting of the aforementioned bis-hydroxyphenyl compound or hydroxyphenyl compound. Therefore, using this polynuclear polyphenol compound as a component material or additive for photosensitive resist will likely improve resolution, etc., while using it as a component material for resin will likely improve heat resistance, flexibility and water resistance, among others.

BEST MODE FOR CARRYING OUT THE INVENTION

In this bis-(hydroxybenzaldehyde) compound expressed by general formula (1) given below as proposed by the present invention, Y represents a bivalent group having a methylene group at both ends, as expressed by general formula (2) or general formula (3) given below.

[Chemical Formula 14]

A bis-(hydroxybenzaldehyde) compound expressed by

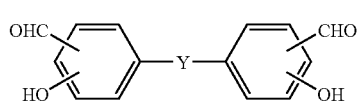

General formula (1)

(wherein Y represents a bivalent group having a methylene group at both ends, as expressed by general formula (2) or general formula (3) given below)

[Chemical Formula 15]

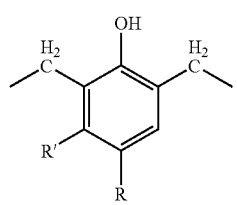

General formula (2)

(wherein R represents an alkyl group with 1 to 4 carbon atoms or cycloalkyl group with 5 or 6 carbon atoms, while R' represents a hydrogen atom or methyl group)

[Chemical Formula 16]

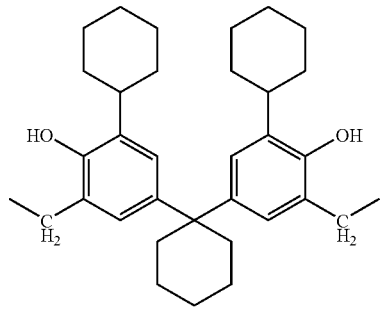

General formula (3)

If Y is expressed by general formula (2) in this bis-(hydroxybenzaldehyde) compound expressed by general formula (1) as proposed by the present invention, in the formula R represents an alkyl group with 1 to 4 carbon atoms or cycloalkyl group with 5 or 6 carbon atoms. Specific examples of an alkyl group with 1 to 4 carbon atoms include a methyl group, ethyl group, n-propyl group, isopropyl group, n-butyl group, 2-butyl group, and t-butyl group, among others. Specific examples of a cycloalkyl group with 5 or 6 carbon atoms include a cyclopentyl group and cyclohexyl group, among others.

Of the above, 2,6-bis-[(formyl-4-hydroxyphenyl)methyl]-4-alkylphenols, where a hydroxy group being a formyl phenol substituted group is present at position 4, can be used favorably. This is because when the bis-(hydroxybenzaldehyde) compound under the present invention is reacted with other phenol to synthesize a polynuclear phenol compound and the obtained polynuclear phenol compound is used as a component material for photosensitive resist composition, then a higher rate of dissolution in alkaline developing solution is anticipated because a compound having a di(4-hydroxyphenyl)methyl group exhibits greater solubility in alkali than a compound having a di(2-hydroxyphenyl)methyl group.

With the bis-(hydroxybenzaldehyde) compound expressed by general formula (1) as proposed by the present invention, therefore, specific examples of a bis-(hydroxybenzaldehyde) compound where Y is expressed by general formula (2) include the following:

2,6-bis-[(3-formyl-4-hydroxyphenyl)methyl]-4-methylphenol (Compound 1),
2,6-bis-[(2-formyl-4-hydroxyphenyl)methyl]-4-methylphenol (Compound 2),
2,6-bis-[(3-formyl-4-hydroxyphenyl)methyl]-4-ethylphenol,
2,6-bis-[(3-formyl-4-hydroxyphenyl)methyl]-4-t-butylphenol,
2,6-bis-[(3-formyl-4-hydroxyphenyl)methyl]-4-sec-butylphenol,
2,6-bis-[(3-formyl-4-hydroxyphenyl)methyl]-4-isopropylphenol,
2,6-bis-[(3-formyl-4-hydroxyphenyl)methyl]-4-n-butylphenol
2,6-bis-[(3-formyl-4-hydroxyphenyl)methyl]-4-n-propylphenol,
2,6-bis-[(5-formyl-2-hydroxyphenyl)methyl]-4-methylphenol (Compound 3),
2,6-bis-[(5-formyl-2-hydroxyphenyl)methyl]-4-ethylphenol, 2,6-bis-[(3-formyl-4-hydroxyphenyl)methyl]-4-cyclopentylphenol, 2,6-bis-[(2-formyl-4-hydroxyphenyl)methyl]-4-cyclopentylphenol, 2,6-bis-[(3-formyl-4-hydroxyphenyl)methyl]-4-cyclohexylphenol (Compound 4), 2,6-bis-[(3-formyl-2-hydroxyphenyl)methyl]-4-cyclohexylphenol, 2,6-bis-[(2-formyl-4-hydroxyphenyl)methyl]-4-cyclohexylphenol (Compound 5), 2,6-bis-[(3-formyl-4-hydroxyphenyl)methyl]-3,4-dimethylphenol, 2,6-bis-[(3-formyl-4-hydroxyphenyl)methyl]-3-methyl-4-t-butylphenol, and 2,6-bis-[(3-formyl-4-hydroxyphenyl)methyl]-3-methyl-4-cyclohexylphenol The structure formulas of sample compounds among the above are given below.

[Chemical Formula 17]

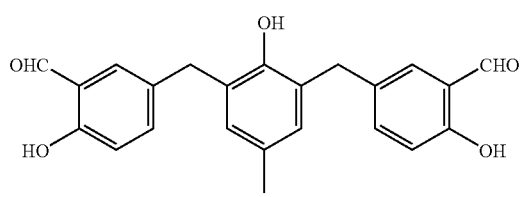
(Compound 1)

[Chemical Formula 18]

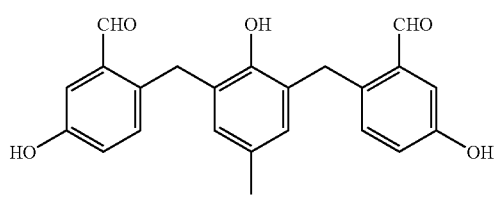
(Compound 2)

[Chemical Formula 19]

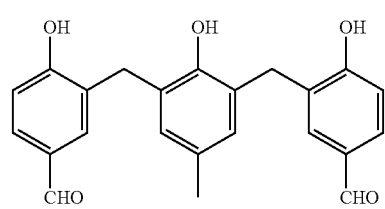
(Compound 3)

[Chemical Formula 20]

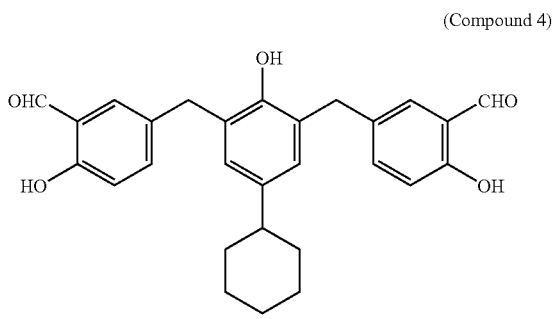
(Compound 4)

[Chemical Formula 21]

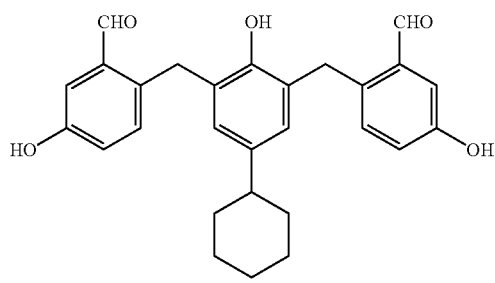
(Compound 5)

Also with the bis-(hydroxybenzaldehyde) compound expressed by general formula (1) as proposed by the present invention, specific examples of a bis-(hydroxybenzaldehyde) compound where Y is expressed by general formula (3) include the following:

1,1-bis-[3-(3-formyl-4-hydroxyphenyl)methyl-4-hydroxy-5-cyclohexylphenyl]cyclohexane (Compound a), 1,1-bis-[3-(3-formyl-2-hydroxyphenyl)methyl-4-hydroxy-5-cyclohexylphenyl]cyclohexane (Compound b), 1,1-bis-[3-(5-formyl-2-hydroxyphenyl)methyl-4-hydroxy-5-cyclohexylphenyl]cyclohexane (Compound c), 1,1-bis-[3-(2-formyl-4-hydroxyphenyl)methyl-4-hydroxy-5-cyclohexylphenyl]cyclohexane (Compound d), and 1-[3-(3-formyl-4-hydroxyphenyl)methyl-4-hydroxy-5-cyclohexylphenyl]-1-[3'-(3'-formyl-2'-hydroxyphenyl)methyl-4'-hydroxy-5'-cyclohexyl phenyl]cyclohexane (Compound e)

Of the above, Compounds a through d where the hydroxybenzaldehyde groups on both ends are symmetrical are preferred, and Compounds a and d having the outer hydroxyl group in the p-position are particularly preferable.

The chemical structure formulas of these compounds are given below.

[Chemical Formula 22]

(Compound a)

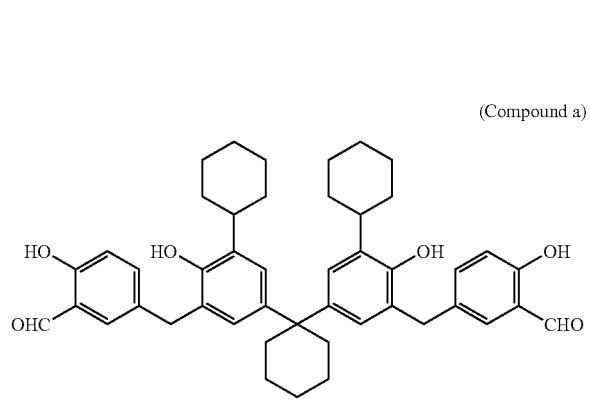

[Chemical Formula 23]

(Compound b)

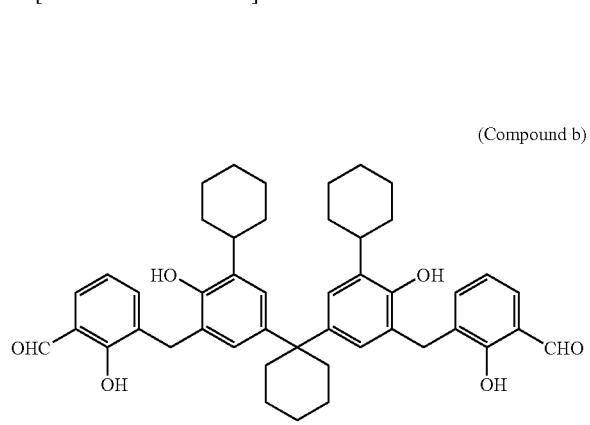

[Chemical Formula 24]

(Compound c)

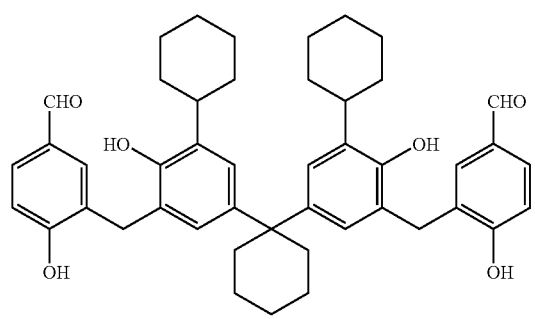

[Chemical Formula 25]

(Compound d)

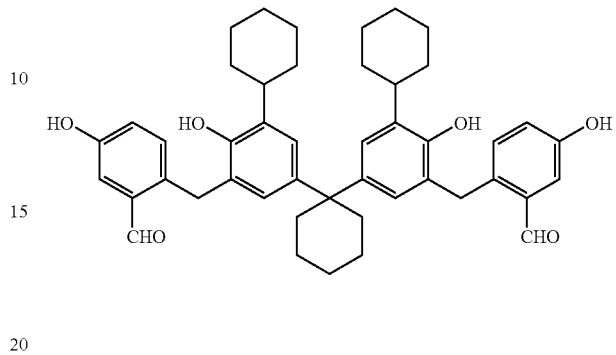

[Chemical Formula 26]

(Compound e)

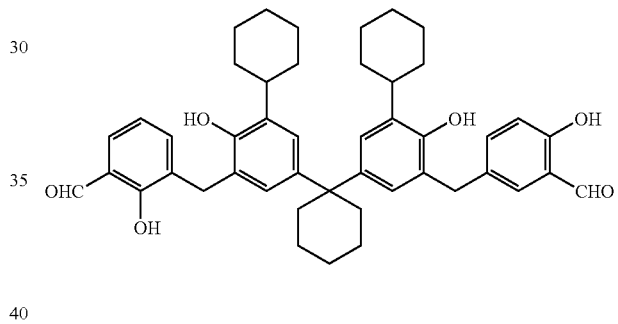

The method for producing this bis-(hydroxybenzaldehyde) compound expressed by general formula (1) as proposed by the present invention is not limited in any way. However, it can be produced by, for example, reacting in the presence of an acid catalyst a 2,6-di(hydroxymethyl)-4-alkylphenol expressed by general formula (12), or a 1,1-bis-(3-cyclohexyl-4-hydroxy-5-hydroxymethylphenyl)cyclohexane expressed by general formula (13), with a hydroxybenzaldehyde.

[Chemical Formula 27]

General formula (12)

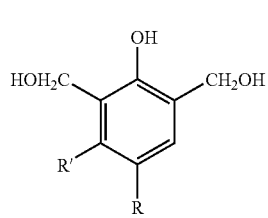

(wherein R and R' represent the corresponding items in general formula (2), respectively)

[Chemical Formula 28]

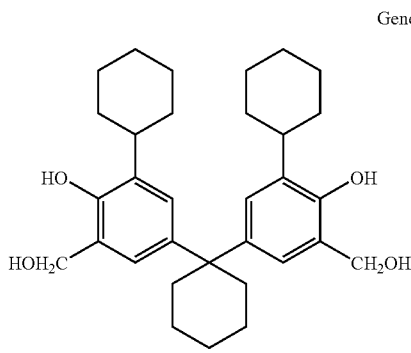

General formula (13)

Specifically with the bis-(hydroxybenzaldehyde) compound expressed by general formula (1) as proposed by the present invention, a bis-(hydroxybenzaldehyde) compound expressed by general formula (4) where Y is expressed by general formula (2) can be obtained by, for example, reacting in the presence of an acid catalyst a 2,6-di(hydroxymethyl)-4-alkylphenol expressed by general formula (12) above, with a hydroxybenzaldehyde.

In the production of the new bis-(hydroxybenzaldehyde) compound expressed by general formula (4) as proposed by the present invention, specific examples of a 2,6-di(hydroxymethyl)-4-alkylphenol expressed by general formula (12) above which is used as a component material include the following:
2,6-di(hydroxymethyl)-4-methylphenol,
2,6-di(hydroxymethyl)-4-ethylphenol,
2,6-di(hydroxymethyl)-4-n-propylphenol,
2,6-di(hydroxymethyl)-4-isopropylphenol,
2,6-di(hydroxymethyl)-4-n-butylphenol,
2,6-di(hydroxymethyl)-4-sec-butylphenol,
2,6-di(hydroxymethyl)-4-t-butylphenol,
2,6-di(hydroxymethyl)-4-cyclopentylphenol,
2,6-di(hydroxymethyl)-4-cyclohexylphenol, and
2,6-di(hydroxymethyl)-3,4-dimethylphenol Also, a hydroxybenzaldehyde used as another component material is expressed by general formula (14) given below, and its specific examples include salicyl aldehyde (also referred to as o-hydroxybenzaldehyde), m-hydroxybenzaldehyde, and p-hydroxybenzaldehyde, among others. Among these, salicyl aldehyde is most preferable.

[Chemical Formula 29]

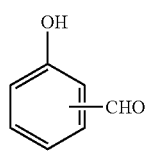

General formula (14)

With regard to the aforementioned method for producing the new bis-(hydroxybenzaldehyde) compound expressed by general formula (4) as proposed by the present invention, the reaction formula that applies when obtaining 2,6-bis-[(3-formyl-4-hydroxyphenyl)methyl]-4-methyl phenol by using 2,6-di(hydroxymethyl)-4-methyl phenol as the component material 2,6-di(hydroxymethyl)-4-alkylphenol, and salicyl aldehyde as the hydroxybenzaldehyde, is given below.

[Chemical Formula 30]

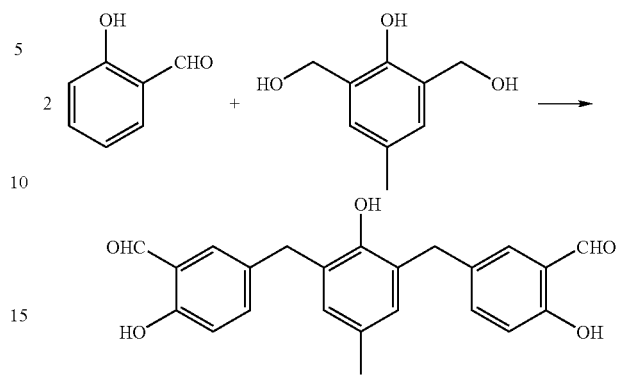

In the reaction of a 2,6-di(hydroxymethyl)-4-alkylphenol expressed by general formula (12) above, with a hydroxybenzaldehyde, the hydroxybenzaldehyde is normally used by 2.1 to 10 mol, or preferably 4 to 6 mol, per 1 mol of the 2,6-di(hydroxymethyl)-4-alkylphenol.

As for the acid catalyst used in the aforementioned reaction, acids of medium strength are preferred. Accordingly, candidate acids include, for example, trifluoroacetic acid, trichloroacetic acid or other halogenated alkyl carbonic acid, phosphoric acid, oxalic acid, nitroalkyl carbonic acid, halogenated benzoic acid, nitro benzoic acid, and weak-acid ion exchanged resin having a carboxyl group, among others. Of these, trifluoroacetic acid, trichloroacetic acid or other halogenated alkyl carbonic acid and phosphoric acid are preferred. In particular, trifluoroacetic acid is preferable because it is liquid and compatible with the material compound.

With the 2,6-di(hydroxymethyl)-4-alkylphenol expressed by general formula (12) above, if a 2,6-di(hydroxymethyl)-4-alkylphenol where the substituent group R is a cycloalkyl group or other group having high hydrophobicity is used as a reaction material, use of trifluoroacetic acid or other halogenated alkyl carbonic acid as an acid catalyst is preferred. If phosphoric acid is used as an acid catalyst, it is preferable to use as a reaction material a 2,6-di(hydroxymethyl)-4-alkylphenol where the substituent group R is a methyl group, ethyl group or propyl group with 1 to 3 carbon atoms or other group having low hydrophobicity. If phosphoric acid is used, in many cases a two-layer reaction is implemented. In these cases, sufficient agitation is needed to improve selectivity.

In the aforementioned reaction, use of hydrochloric acid, sulfuric acid, sulfuric anhydrite, p-toluene sulfonic acid or any other strong acid as an acid catalyst is not preferred, because the material hydroxybenzaldehyde will undergo self-reaction and produce resins and other byproducts, consequently making it difficult to retrieve the target product or reducing the yield significantly.

These acid catalysts are not specifically limited in terms of how much they should be used. Normally, however, the acid catalyst is used by 0.1 to 10 mol, or preferably 0.3 to 4 mol, per 1 mol of hydroxybenzaldehyde, for example.

In the aforementioned reaction, there is no need to use any reaction solvent. In certain situations, however, such as when any material or catalyst is solid, or when the reaction liquid is very viscous and cannot be agitated sufficiently, or when the materials do not mix well with the catalyst, a reaction solvent may be used as deemed necessary.

There are no specific limitations and any reaction solvent may be used as long as it does not inhibit the reaction. However, candidates include isopropyl ketone, methyl ethyl ketone, methyl isobutyl ketone, diisopropyl ketone and other aliphatic ketones, toluene, xylene, cumene, benzene and other aromatic hydrocarbons, acetic acid, and ether, among others, where an appropriate solvent should be selected by considering each reaction material used, solubility of the obtained product, reaction conditions, ease of mixing of the material and catalyst, economy of the reaction, and the like. These reaction solvents are normally used by 0.1 to 5 parts by weight, or preferably 0.5 to 2 parts by weight, with respect to hydroxybenzaldehyde. However, the amount of reaction solvent is not limited at all to the above ranges.

If salicyl aldehyde is used as the material hydroxybenzaldehyde, for example, normally no solvent is necessary. If the reaction liquid is viscous and agitation is difficult, however, it is better to use a solvent as deemed appropriate. If m-hydroxybenzaldehyde or p-hydroxybenzaldehyde having a high melting point is used, it is necessary to use a solvent as deemed appropriate.

The reaction temperature is normally in a range of 0 to 80° C., or preferably in a range of 10 to 70° C. To be specific, an ideal temperature range is 40 to 65° C. if the acid catalyst is phosphoric acid, or 20 to 40° C. if the acid catalyst is trifluoroacetic acid.

Normally, the reaction should be implemented for around 5 to 50 hours under agitation under nitrogen flow.

There is no specific way to add the reaction materials. However, the method to add 2,6-di(hydroxymethyl)-4-alkyl phenol to a mixed solution containing hydroxybenzaldehyde and acid catalyst is preferred in industrial settings. In this case, addition should be implemented over a period of 1 to 10 hours or so.

In the aforementioned reaction, normally the resulting bis-(hydroxybenzaldehyde) compound contains various byproducts such as isomers in addition to the target compound. Therefore, it is desirable to refine the resulting product using crystallization or by other means.

As for the refining method, one example is to add ammonia water, aqueous sodium hydroxide solution or other alkaline water to the obtained reaction liquid to neutralize the acid catalyst after the reaction has completed. If necessary in the next water-layer separation process because no reaction solvent is used or for other reason, a solvent that can be separated from water, such as toluene, xylene, methyl isobutyl ketone or diethyl ether, may be added (this solvent may be added before the neutralization). Thereafter, the water layer is separated and the oil layer is washed with water, and the obtained oil layer is distilled to remove the solvent, and if necessary, hydroxybenzaldehyde. Then, a crystallization solvent is added to cause crystallization to obtain coarse crystal. This operation may be repeated several times, if necessary.

The obtained coarse crystal may be refined further, if necessary.

For example, this coarse crystal is dissolved in aromatic hydrocarbon, aliphatic ketone, or a mixed solvent containing the two, and the obtained solution is washed with ion exchanged water, after which the obtained oil layer is condensed and a crystallization solvent is added to cause crystallization again, and the obtained crystal is filtered and dried to obtain the target bis-(formyl phenol) compound with high purity.

The new bis-(formylphenol) compound expressed by general formula (4) as proposed by the present invention has three phenolic hydroxyl group and two phenolic aldehyde groups in the molecule. Accordingly, the reactivities of these functional groups can be utilized to make this bis-(formylphenol) compound an intermediate reaction material that can be used with ease. For example, the reactivities of the two formyl groups at the ends of the molecule can be utilized by reacting a phenol in the presence of a hydrochloric acid or other acid catalyst to obtain 2,6-bis-[di(hydroxyphenyl)methyl-hydroxyphenyl]methyl}-4-alkylphenol and other polynuclear phenol compounds. These compounds are useful, just like any other bis-(hydroxybenzaldehyde) compound conforming to the present invention, for use as component materials for various functional materials or component materials for photo resists for semiconductors, among others.

With the bis-(hydroxybenzaldehyde) compound expressed by general formula (1) as proposed by the present invention, the new bis-(hydroxybenzaldehyde) compound expressed by general formula (7) where Y is expressed by general formula (3) above can be produced by, for example, reacting in the presence of an acid catalyst a 1,1-bis-(3-cyclohexyl-4-hydroxy-5-hydroxymethylphenyl)cyclohexane expressed by formula (13) given below, with a hydroxybenzaldehyde expressed by general formula (14).

[Chemical Formula 31]

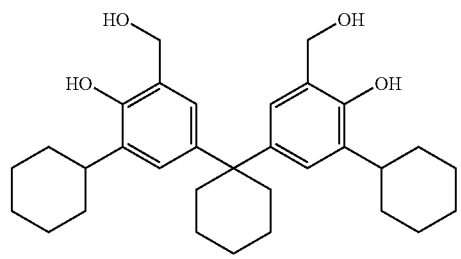

Formula (13)

[Chemical Formula 32]

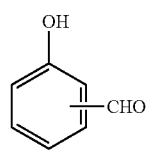

General formula (14)

With the bis-(hydroxybenzaldehyde) compound expressed by general formula (1) as proposed by the present invention, the hydroxybenzaldehyde expressed by general formula (14) above is specifically salicyl aldehyde, m-hydroxybenzaldehyde or p-hydroxybenzaldehyde when producing the bis-(hydroxybenzaldehyde) compound expressed by general formula (7) where Y is expressed by general formula (3) above. Among these, salicyl aldehyde is most preferable.

In the reaction of a 1,1-bis-(3-cyclohexyl-4-hydroxy-5-hydroxymethylphenyl)cyclohexane expressed by formula (13) above with a hydroxybenzaldehyde, the hydroxybenzaldehyde is normally used by 4 to 20 mol, or preferably 7 to 13 mol, per 1 mol of the 1,1-bis-(3-cyclohexyl-4-hydroxy-5-hydroxymethylphenyl)cyclohexane. If the mol ratio is too low, the target reaction product will react further with the hydroxymethyl group of 1,1-bis-(3-cyclohexyl-4-hydroxy-5-hydroxymethylphenyl)cyclohexane to reduce the selectivity. The reaction liquid itself will be polymerized and the molecular weight will increase, which also makes it difficult to obtain the target product with high purity and is not desirable.

As for the acid catalyst used in the aforementioned reaction, acids of medium strength are preferred. Accordingly, candidate acids include, for example, trifluoroacetic acid, trichloroacetic acid or other halogenated alkyl carbonic acid, phosphoric acid, oxalic acid, nitroalkyl carbonic acid, halogenated benzoic acid, and nitro benzoic acid, among others. Of these, trifluoroacetic acid, trichloroacetic acid or other halogenated alkyl carbonic acid is preferred. In particular, trifluoroacetic acid is preferable because it is liquid and compatible with the material compound.

These acid catalysts are not specifically limited in terms of how much they should be used. Normally, however, the acid catalyst is used by 0.5 to 10 mol per 1 mol of 1,1-bis-(3-cyclohexyl-4-hydroxy-5-hydroxymethylphenyl)cyclohexane, for example.

In the aforementioned reaction, use of hydrochloric acid, sulfuric acid, sulfuric anhydrite, p-toluene sulfonic acid or any other strong acid as an acid catalyst is not preferred, because the material hydroxybenzaldehyde will undergo self-reaction and produce resins and other byproducts, consequently making it difficult to retrieve the target substance or reducing the yield significantly.

Also in the aforementioned reaction, there is no need to use any reaction solvent. In certain situations, however, such as when any material or catalyst is solid, or when the reaction liquid is very viscous and cannot be agitated sufficiently, a reaction solvent may be used as deemed necessary.

There are no specific limitations and any reaction solvent may be used as long as it does not inhibit the reaction. However, candidates include isopropyl ketone, methyl ethyl ketone, methyl isobutyl ketone, diisopropyl ketone and other aliphatic ketones, toluene, xylene, cumene, benzene and other aromatic hydrocarbons, and acetic acid, among others, where an appropriate solvent should be selected by considering each reaction material used, solubility of the obtained product, reaction conditions, economy of the reaction, and the like. These reaction solvents are normally used by 0.1 to 5 times by weight, or preferably 0.5 to 2 times by weight, with respect to hydroxybenzaldehyde. However, the amount of reaction solvent is not limited at all to the above ranges.

The reaction temperature is normally in a range of 0 to 60° C., or preferably in a range of 10 to 50° C., or more preferably in a range of 20 to 40° C. Normally, the reaction should be implemented for around 5 to 40 hours under agitation under nitrogen flow.

In industrial production settings, it is sufficient to add 1,1-bis-(3-cyclohexyl-4-hydroxy-5-hydroxymethylphenyl)cyclohexane to a mixed solution containing benzaldehyde and acid catalyst, over a period of normally around 0.5 to 20 hours, or preferably around 2 to 10 hours, and then agitate further for around 10 to 50 hours at the same temperature to cause reaction, as explained in the examples.

In the aforementioned reaction, normally the resulting bis-(hydroxybenzaldehyde) compound contains various byproducts such as isomers in addition to the target compound. Therefore, it is desirable to refine the resulting product using crystallization or by other means.

As for the refining method, one example is to add ammonia water, aqueous sodium hydroxide solution or other alkaline water to the obtained reaction liquid after the reaction has completed to neutralize the acid catalyst to approx. pH5 to 7. If necessary in the next water-layer separation process because no reaction solvent is used or for other reason, a solvent that can be separated from water, such as toluene, xylene, methyl isobutyl ketone or ether, may be added (this solvent may be added before the neutralization). Thereafter, the water layer is separated and the oil layer is washed with water, and the obtained oil layer is distilled to remove the solvent, and if necessary, hydroxybenzaldehyde. Then, a crystallization solvent is added to cause crystallization to obtain coarse crystal. This operation may be repeated several times, if necessary.

As a result of the above, the target bis-(hydroxybenzaldehyde) compound expressed by general formula (7) can be obtained with high purity.

Any crystallization solvent can be selected as deemed appropriate for use in the aforementioned refining method, according to the crystallization conditions, refining effect, economy, and the like. For examples, candidate aromatic hydrocarbons include toluene, xylene and cumene, among others. Candidate ketones include isopropyl ketone, methyl ethyl ketone, methyl isobutyl ketone and diisopropyl ketone, while candidate aliphatic hydrocarbons include n-pentane, n-hexane, n-heptane, and cyclohexane, for example.

Next, the polynuclear polyphenol compound expressed by general formula (8), which is another new compound under the present invention as derived from the bis-(hydroxybenzaldehyde) compound proposed by the present invention, is explained. First, specific examples of a polynuclear polyphenol compound expressed by general formula (10), where Y in general formula (8) is expressed by general formula (2) above, include the following:

2,6-bis-{[3-di(4-hydroxy-2,5-dimethylphenyl)methyl-4-hydroxyphenyl]methyl}-4-methylphenol (Compound A),
2,6-bis-{[3-di(4-hydroxy-2,3,5-trimethylphenyl)methyl-4-hydroxyphenyl]methyl}-4-methyl phenol (Compound B),
2,6-bis-{[3-di(4-hydroxy-3,5-dimethylphenyl)methyl-4-hydroxyphenyl]methyl}-4-methyl phenol (Compound C),
2,6-bis-{[3-di(4-hydroxyphenyl)methyl-4-hydroxyphenyl]methyl}-4-methylphenol (Compound D),
2,6-bis-{[3-di(4-hydroxy-3-isopropylphenyl)methyl-4-hydroxyphenyl]methyl}-4-methylphenol (Compound E),
2,6-bis-{[3-di(4-hydroxy-2-methyl-5-t-butylphenyl)methyl-4-hydroxyphenyl]methyl}-4-methylphenol (Compound F),
2,6-bis-{[3-di(4-hydroxy-3-methylphenyl)methyl-4-hydroxyphenyl]methyl}-4-methylphenol,
2,6-bis-{[3-di(4-hydroxy-2-methylphenyl)methyl-4-hydroxyphenyl]methyl}-4-methylphenol,
2,6-bis-{[3-di(4-hydroxy-3-t-butylphenyl)methyl-4-hydroxyphenyl]methyl}-4-methylphenol,
2,6-bis-{[3-di(4-hydroxy-3-sec-butylphenyl)methyl-4-hydroxyphenyl]methyl}-4-methylphenol,
2,6-bis-{[3-di(3-cyclohexyl-4-hydroxyphenyl)methyl-4-hydroxyphenyl]methyl}-4-methylphenol,
2,6-bis-{[3-di(3-cyclohexyl-4-hydroxy-5-methylphenyl)methyl-4-hydroxyphenyl]methyl}-4-methylphenol,
2,6-bis-{[3-di(5-cyclohexyl-4-hydroxy-2-methylphenyl)methyl-4-hydroxyphenyl]methyl}-4-methylphenol (Compound G),
2,6-bis-{[3-di(4-hydroxy-2,5-dimethylphenyl)methyl-4-hydroxyphenyl]methyl}-4-ethylphenol,
2,6-bis-{[3-di(4-hydroxy-2,5-dimethylphenyl)methyl-4-hydroxyphenyl]methyl}-4-isopropylphenol,
2,6-bis-{[3-di(4-hydroxy-2,5-dimethylphenyl)methyl-4-hydroxyphenyl]methyl}-4-cyclohexylphenol,
2,6-bis-{[3-di(4-hydroxy-2-methyl-5-cyclohexylphenyl)methyl-4-hydroxyphenyl]methyl}-4-cyclohexylphenol,
2,6-bis-{[3-di(4-hydroxy-2,5-dimethylphenyl)methyl-4-hydroxyphenyl]methyl}-3,4-dimethylphenol,
2,6-bis-{[3-di(4-hydroxy-2,5-dimethylphenyl)methyl-4-hydroxyphenyl]methyl}-3-methyl-4-t-butylphenol,
2,6-bis-{[3-di(4-hydroxy-2,5-dimethylphenyl)methyl-4-hydroxyphenyl]methyl}-3-methyl-4-cyclohexylphenol, and
2,6-bis-{[3-di(4-hydroxy-2-methyl-5-cyclohexylphenyl)methyl-4-hydroxyphenyl]methyl}-3,4-dimethylphenol The chemical structure formulas of Compounds A through G above are given below.
[Chemical Formula 33]
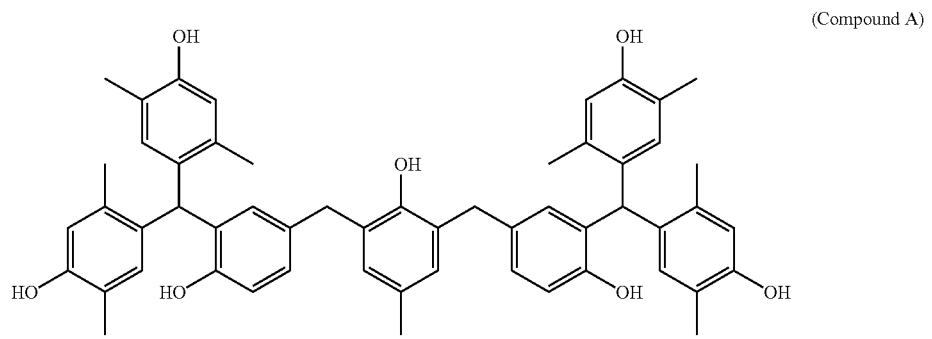
(Compound A)
[Chemical Formula 34]
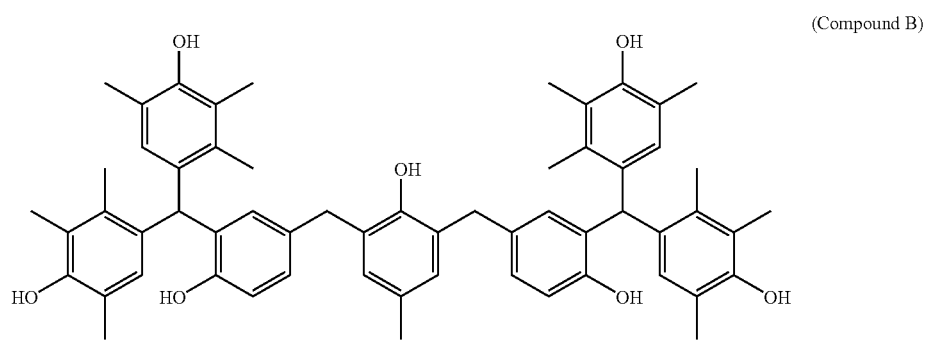
(Compound B)
[Chemical Formula 35]
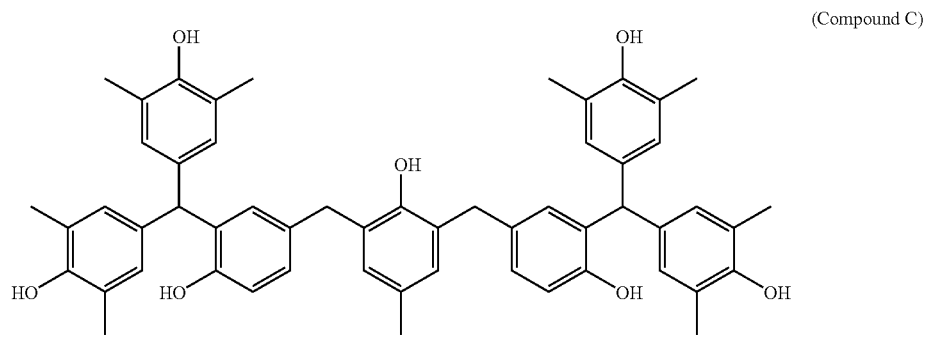
(Compound C)

[Chemical Formula 36]
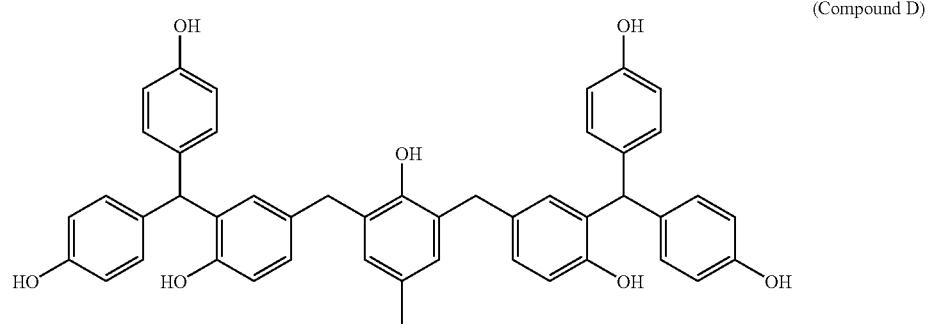
(Compound D)
[Chemical Formula 37]
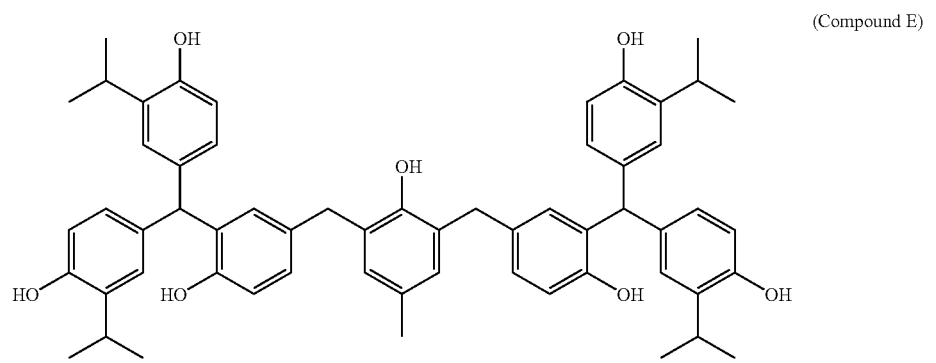
(Compound E)
[Chemical Formula 38]
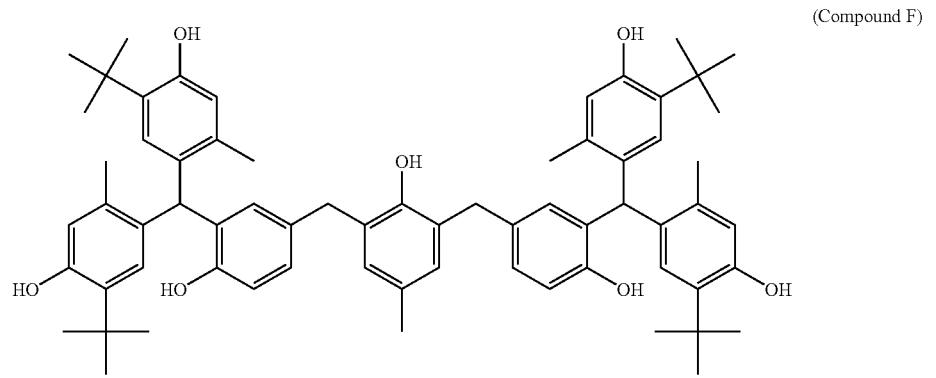
(Compound F)

[Chemical Formula 39]

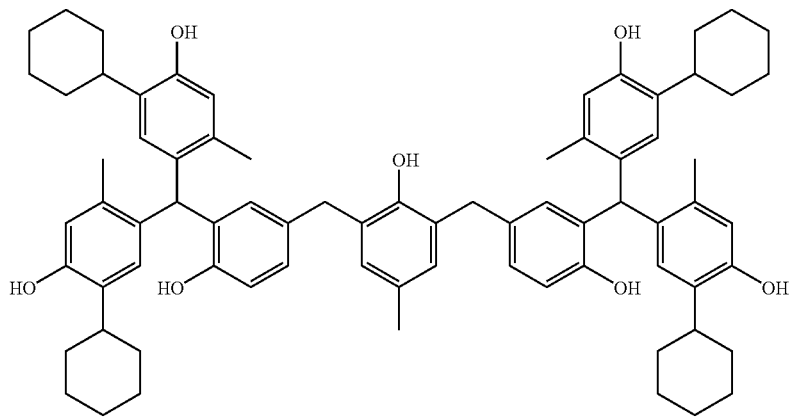

(Compound G)

With the polynuclear polyphenol compound expressed by general formula (8), specific examples of a polynuclear polyphenol compound expressed by general formula (11) where Y is expressed by general formula (3) include the following:

1,1-bis-{3-(3-[bis-(4-hydroxy-2,5-dimethylphenyl)methyl]-4-hydroxyphenyl)methyl-4-hydroxy-5-cyclohexylphenyl}cyclohexane (Compound H), 1,1-bis-{3-(3-[bis-(4-hydroxy-2,3,5-trimethylphenyl)methyl]-4-hydroxyphenyl)methyl-4-hydroxy-5-cyclohexylphenyl}cyclohexane (Compound 1), 1,1-bis-{3-(3-[bis-(4-hydroxy-3,5-dimethylphenyl)methyl]-4-hydroxyphenyl)methyl-4-hydroxy-5-cyclohexylphenyl}cyclohexane (Compound J), 1,1-bis-{3-(3-[bis-(4-hydroxyphenyl)methyl]-4-hydroxyphenyl)methyl-4-hydroxy-5-cyclohexylphenyl}cyclohexane (Compound K), 1,1-bis-{3-(3-[bis-(4-hydroxy-3-isopropylphenyl)methyl]-4-hydroxyphenyl)methyl-4-hydroxy-5-cyclohexylphenyl}cyclohexane (Compound L), 1,1-bis-{3-(3-[bis-(4-hydroxy-2-methyl-5-t-butylphenyl)methyl]-4-hydroxyphenyl)methyl-4-hydroxy-5-cyclohexylphenyl}cyclohexane (Compound M), and 1,1-bis-{3-(3-[bis-(5-cyclohexyl-4-hydroxy-2-methylphenyl)methyl]-4-hydroxyphenyl)methyl-4-hydroxy-5-cyclohexylphenyl}cyclohexane (Compound N), as well as 1,1-bis-{3-(3-[bis-(4-hydroxy-3-methylphenyl)methyl]-4-hydroxyphenyl)methyl-4-hydroxy-5-cyclohexylphenyl}cyclohexane, 1,1-bis-{3-(3-[bis-(4-hydroxy-2-methylphenyl)methyl]-4-hydroxyphenyl)methyl-4-hydroxy-5-cyclohexylphenyl}cyclohexane, 1,1-bis-{3-(3-[bis-(4-hydroxy-3-t-butylphenyl)methyl]-4-hydroxyphenyl)methyl-4-hydroxy-5-cyclohexylphenyl}cyclohexane, 1,1-bis-{3-(3-[bis-(4-hydroxy-3-sec-butylphenyl)methyl]-4-hydroxyphenyl)methyl-4-hydroxy-5-cyclohexylphenyl}cyclohexane, 1,1-bis-{3-(3-[bis-(5-cyclohexyl-4-hydroxy-3-methylphenyl)methyl]-4-hydroxyphenyl)methyl-4-hydroxy-5-cyclohexylphenyl}cyclohexane, and 1,1-bis-{3-(3-[bis-(3-cyclohexyl-4-hydroxyphenyl)methyl]-4-hydroxyphenyl)methyl-4-hydroxy-5-cyclohexylphenyl}cyclohexane The chemical structure formulas of Compounds H through N above are given below.

[Chemical Formula 40]

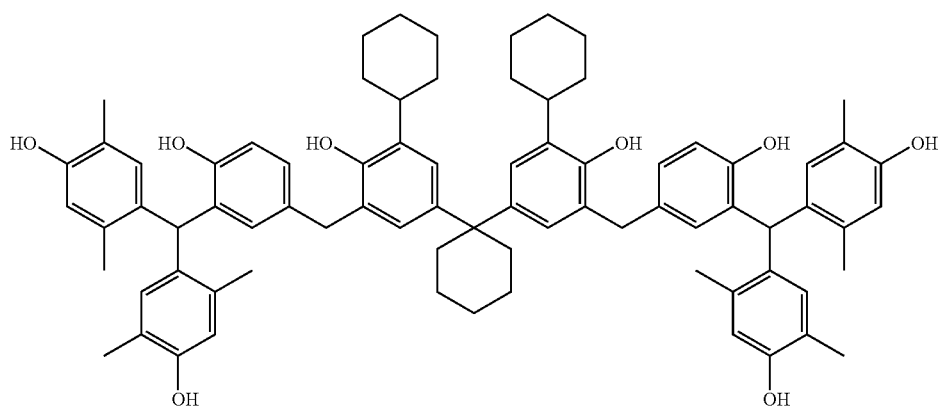

(Compound H)

[Chemical Formula 41]
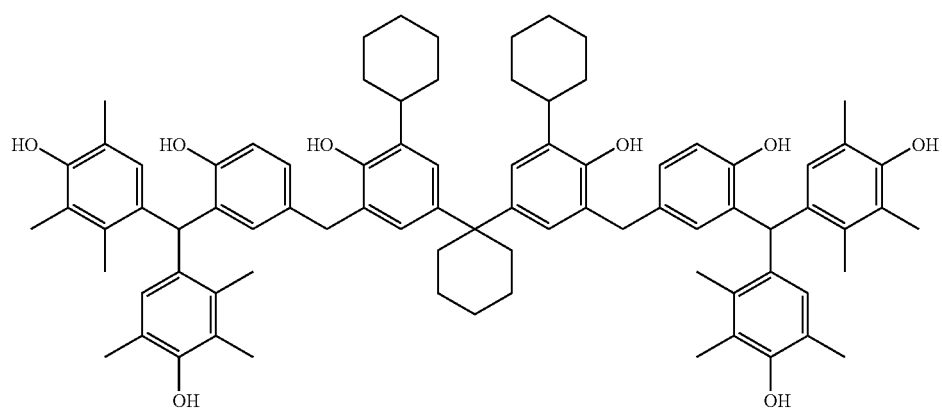
(Compound I)
[Chemical Formula 42]
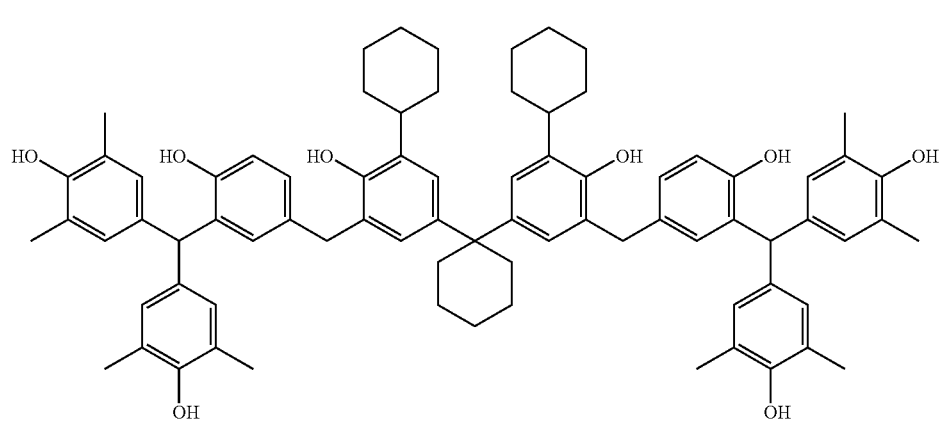
(Compound J)
[Chemical Formula 43]
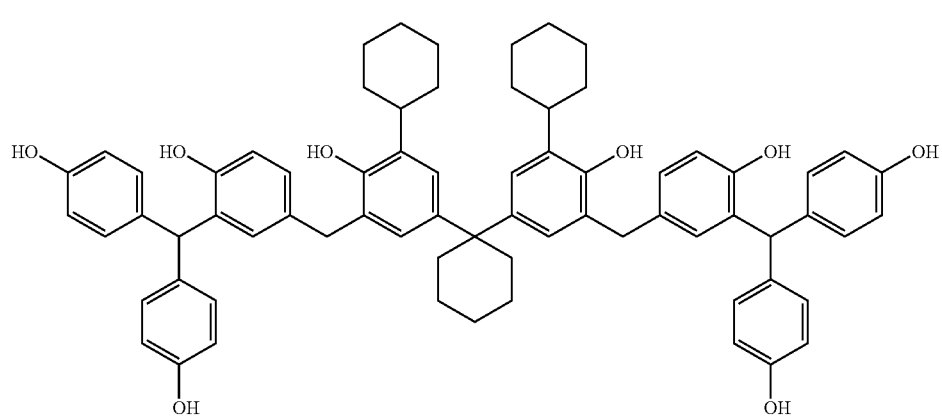
(Compound K)

[Chemical Formula 44]
(Compound L)
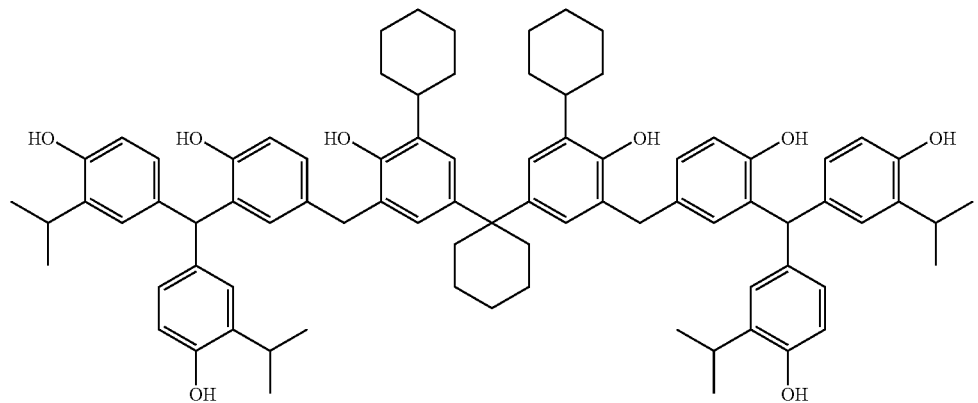
[Chemical Formula 45]
(Compound M)
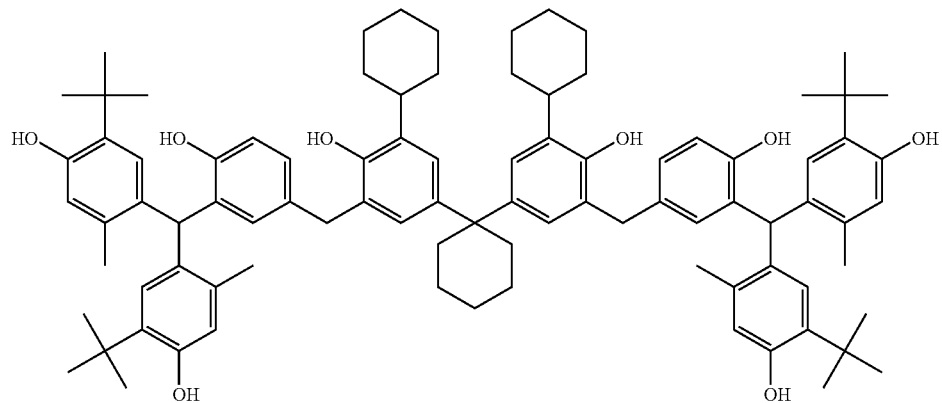
[Chemical Formula 46]
(Compound N)
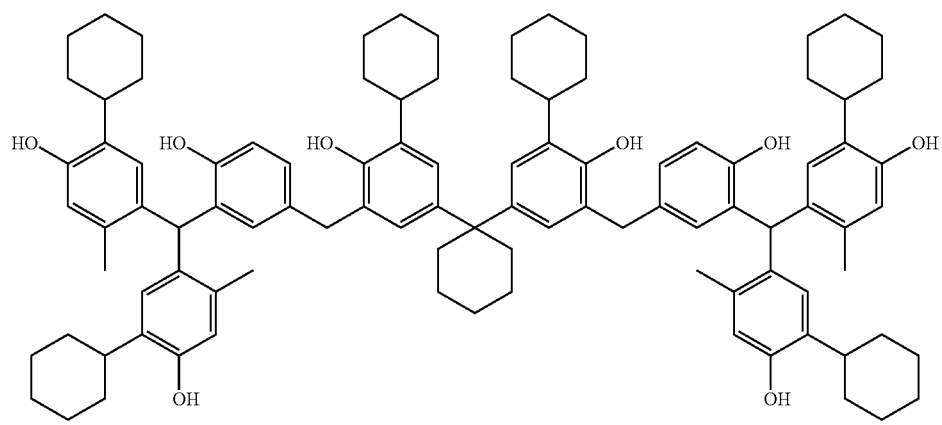

The method for producing the new polynuclear polyphenol compound expressed by general formula (8) as proposed by the present invention is not limited in any way. However, it can be produced by, for example, reacting in the presence of an acid catalyst the aforementioned bis-(hydroxybenzaldehyde) compound expressed by general formula (1) as proposed by the present invention, with a phenol expressed by general formula (15) given below.

[Chemical Formula 47]

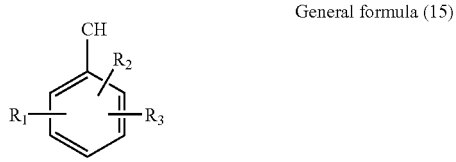

General formula (15)

(wherein $R_1$, $R_2$, and $R_3$ represent the corresponding items in general formula (9), respectively, each being an independent hydrogen atom, alkyl group with 1 to 4 carbon atoms, or cycloalkyl group with 5 or 6 carbon atoms; however, they are not substituted in position 4 with respect to the hydroxyl group)

In the aforementioned method for producing polynuclear polyphenol compound proposed by the present invention, the phenol substituent group expressed by general formula (15) above should preferably be an alkyl group with 1 or 2 carbon atoms or cyclohexyl group, and the number of substituent groups should preferably be 2.

Specific examples of a phenol expressed by general formula (15) above include phenol, 2,5-xylenol, O-cresol, m-cresol, 2,3,6-trimethylphenol, O-t-butylphenol, 2-isopropylphenol, 2-t-butyl-5-methylphenol, 2-t-butyl-6-methylphenol, 2-cyclohexylphenol, and 2-cyclohexyl-5-methylphenol, among others.

Given below are the examples of the reaction formulas to obtain the aforementioned Compound a, or 1,1-bis-[3-(3-formyl-4-hydroxyphenyl)methyl-4-hydroxy-5-cyclohexylphenyl]cyclohexane (Compound a) which is a new bis-(hydroxybenzaldehyde) compound conforming to the present invention, by reacting salicyl aldehyde with 1,1-bis-(3-cyclohexyl-4-hydroxy-5-hydroxymethylphenyl)cyclohexane, and then react the obtained 1,1-bis-[3-(3-formyl-4-hydroxyphenyl)methyl-4-hydroxy-5-cyclohexylphenyl]cyclohexane (Compound a) with 2,5-dimethyl phenol to obtain a polynuclear polyphenol compound being 1,1-bis-{3-(3-[bis-(4-hydroxy-2,5-dimethylphenyl)methyl]-4-hydroxyphenyl)methyl-4-hydroxy-5-cyclohexylphenyl}cyclohexane (Compound H).

[Chemical Formula 48]
[Chemical Formula 49]

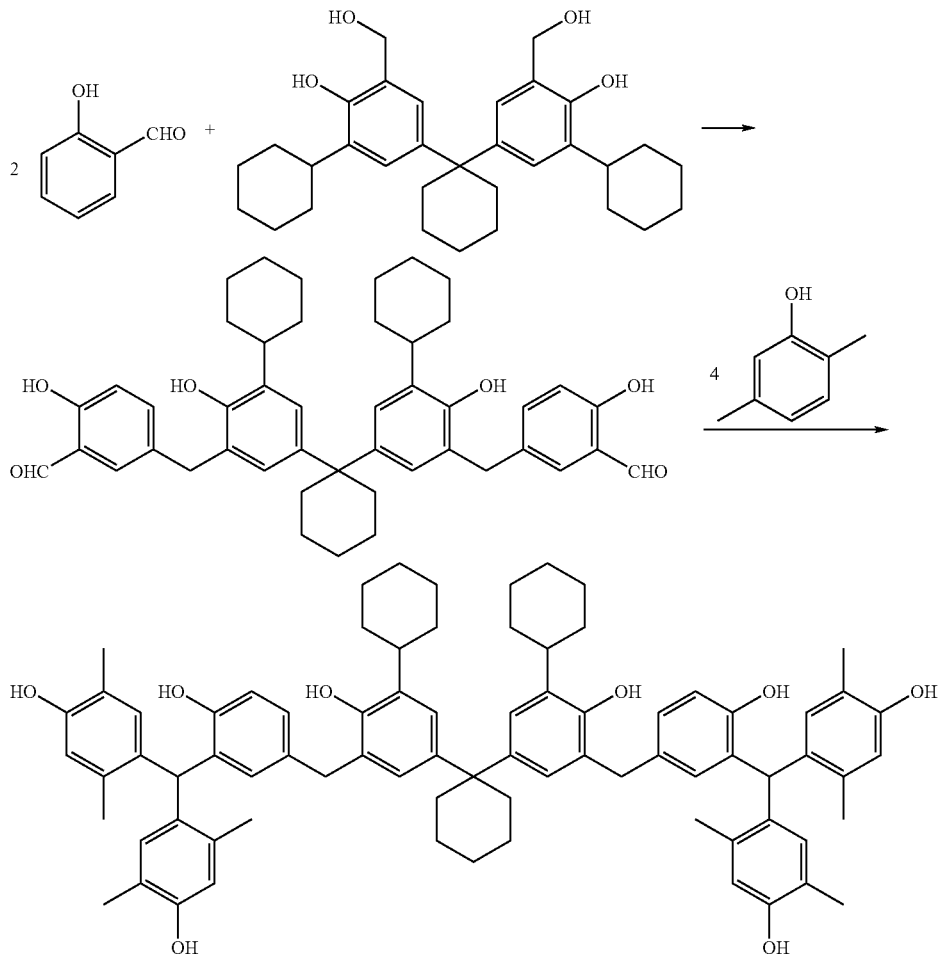

In the aforementioned method for producing a polynuclear polyphenol compound expressed by general formula (8) proposed by the present invention, the reaction of a bis-(hydroxybenzaldehyde) compound expressed by general formula (1) in conformance with the present invention, such as the aforementioned 1,1-bis-[3-(3-formyl-4-hydroxyphenyl)methyl-4-hydroxy-5-cyclohexylphenyl]cyclohexane, with a phenol expressed by general formula (15) above, should normally use the phenol by 4 to 15 mol, or preferably 4.2 to 6 mol, per 1 mol of the bis-(hydroxybenzaldehyde) compound expressed by general formula (1) according to the present invention.

As another example, the reaction of a 2,6-bis-[(3-formyl-4-hydroxyphenyl)methyl]-4-alkylphenol expressed by the structure given below, with a phenol expressed by general formula (15) above, should normally use the phenol by an amount in the same ranges as described above with respect to the 2,6-bis-[(3-formyl-4-hydroxyphenyl)methyl]-4-alkylphenol.

[Chemical Formula 50]

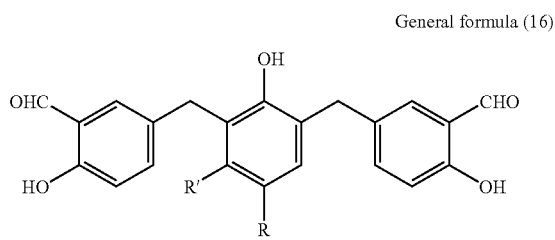

General formula (16)

(wherein R and R' represent the corresponding items in general formula (2), respectively)

If the mol ratio is too low, four molecules of the phenol will not bond with one molecule of the bis-(hydroxybenzaldehyde) compound, which will cause generation of byproducts to increase. As a result, the selectivity will drop and the target product cannot be obtained with high purity, which is not desirable.

Specific examples of an acid catalyst used in the aforementioned production method include concentrated hydrochloric acid, sulfuric acid, p-toluene sulfonic acid, methane sulfonic acid, trifluoromethane sulfonic acid, oxalic acid, phosphoric acid, and trifluoroacetic acid, among others. Of these, concentrated hydrochloric acid is preferable because it allows the target product to be obtained at a relatively high yield. Although the specific amount of acid catalyst varies depending on the type of catalyst, normally the acid catalyst should account for 5 to 50 percent by weight, or preferably 10 to 30 percent by weight, with respect to the amount of phenol introduced. In the case of a polynuclear polyphenol compound expressed by general formula (8) where Y is a compound expressed by general formula (3), the molecule may be cut at the center due to an acid, and therefore an excessive acid concentration is not desirable in this case because the reaction selectivity will drop.

In the aforementioned production method, there is no need to use any reaction solvent. In certain situations, however, such as when any material or catalyst is solid, or when the reaction liquid is viscous and cannot be agitated sufficiently, a reaction solvent may be used as deemed necessary.

There are no specific limitations and any reaction solvent may be used as long as it does not inhibit the reaction. However, candidates include isopropyl ketone, methyl ethyl ketone, methyl isobutyl ketone, diisopropyl ketone and other aliphatic ketones, toluene, xylene, cumene, benzene and other aromatic hydrocarbons, and methanol, ethanol, isopropyl alcohol, n-propyl alcohol, t-butyl alcohol, isobutyl alcohol, n-butyl alcohol and other lower aliphatic alcohols, among others, where an appropriate solvent should be selected by considering each reaction material used, solubility of the obtained product, reaction conditions, economy of the reaction, and the like. Among others, aliphatic ketones and lower aliphatic alcohols are preferred, and methanol is particularly preferable. These reaction solvents are normally used by 0.1 to 5 times by weight, or preferably 0.5 to 2 times by weight, with respect to phenol. However, the amount of reaction solvent is not limited at all to the above ranges.

The reaction should normally be implemented for around 2 to 50 hours under agitation under nitrogen flow at a temperature in a range of 0 to 100° C., or preferably in a range of 30 to 50° C.

In the aforementioned production method, normally the resulting polynuclear polyphenol compound contains various byproducts such as isomers in addition to the target compound. Therefore, it is desirable to refine the resulting product using crystallization or by other means. As for the refining method, one example is to add ammonia water, aqueous sodium hydroxide solution or other alkaline water to the obtained reaction liquid after the reaction has completed to neutralize the acid catalyst to approx. pH5 to 7. Thereafter, the water layer is separated and the oil layer is washed with water, and the obtained oil layer is distilled to remove the solvent, and if necessary, phenol. Then, a crystallization solvent is added to cause crystallization to obtain coarse crystal. The obtained coarse crystal may be refined further, if necessary.

For example, this coarse crystal is dissolved in aromatic hydrocarbon, aliphatic ketone, or a mixed solvent containing the two, and the obtained solution is washed with ion exchanged water, after which the obtained oil layer is condensed and a crystallization solvent is added to cause crystallization again, and the obtained crystal is filtered and dried to obtain the target polynuclear polyphenol compound with high purity.

EXAMPLES

Each new compound conforming to the present invention is explained in further details using an example.

Example 1

Synthesis of 2,6-bis-[(3-formyl-4-hydroxyphenyl) methyl]-4-methylphenol (Compound 1)

Into a nitrogen-substituted 1-liter four-way flask equipped with a reflux condenser, thermometer and agitator, 244.0 g (2.0 mol) of salicyl aldehyde was introduced and then 244.0 g (1.87 mol) of 75% aqueous phosphoric acid solution was drip-fed and mixed under agitation over a period of 30 minutes at room temperature. Into the mixed solution, 84.0 g (0.5 mol) of 2,6-di(hydroxymethyl)-4-methylphenol powder was added intermittently over a period of 6 hours at a temperature of 60° C., and after the entire amount had been added the mixture was agitated further for 17 hours at the same temperature to cause reaction.

After the reaction had completed, 366 g of methyl isobutyl ketone was added to the reacted mixed solution, after which the water layer was separated by means of oil-water separation, and the oil layer containing the target product was obtained. The obtained oil layer was neutralized in 16% aqueous sodium hydroxide solution, after which 150 g of water was added and the mixture was heated to 80° C. Thereafter, the water layer was separated and the obtained oil layer was mixed with water again, followed by water washing and separation according to the same procedure above. The obtained oil layer was decompressed and condensed to 20 mmHg at 160° C., and 94 g of methyl isobutyl ketone was added to the concentrate at a temperature of 120° C. Then, 470 g of toluene was added at a temperature of 110° C. to cause crystallization. The crystallization liquid was cooled and the precipitated crystal was filtered to obtain 160.6 g of coarse crystal containing the solvent. This coarse crystal was again introduced to a 1-liter four-way flask and dissolved by adding 240 g of methyl isobutyl ketone. The obtained solution was condensed at normal pressure and 184 g of toluene was added to the concentrate, and the resulting concentrate was condensed again at normal pressure. Then, 240 g of toluene was added to the obtained concentrate to cause crystallization again.

The crystallization liquid was cooled and the precipitated crystal was filtered and dried to obtain 89.7 g of the target product, or 2,6-bis-[(3-formyl-4-hydroxyphenyl)methyl]-4-methylphenol, as a white to yellowish powder crystal with a purity of 95.8% (measured by high-speed liquid chromatography).

The yield with respect to 2,6-di(hydroxymethyl)-4-methylphenol was 47.7%.

Mass spectrometry LC-MS (APCI$^-$)

Analysis result: Molecular weight 375 (M-H)$^-$

Melting point (differential thermal analysis): 145.6° C.

Proton nuclear magnetic resonance spectrum (400 Mz, solvent: DMSO-d6)

TABLE 1

| ppm | Assignment | Signal pattern | Number of protons |
|---|---|---|---|
| 10.54 | —CHO | s | 2 |
| 10.23 | Ph—OH | s | 2 |
| 8.31 | Ph—OH | s | 1 |
| 7.48-6.73 | Ph—H | m | 8 |
| 3.86 | —CH$_2$ | s | 4 |
| 2.11 | —CH$_3$ | s | 3 |

Example 2

Synthesis of 2,6-bis-[(3-formyl-4-hydroxyphenyl) methyl]-4-cyclohexylphenol (Compound 4)

Into a nitrogen-substituted 1-liter four-way flask equipped with a reflux condenser, thermometer and agitator, 183.0 g (1.5 mol) of salicyl aldehyde was introduced and then 85.8 g (0.75 mol) of trifluoroacetic acid was drip-fed and mixed under agitation over a period of 30 minutes at room temperature. Into the mixed solution, 70.8 g (0.3 mol) of 2,6-di (hydroxymethyl)-4-cyclohexylphenol powder was added intermittently over a period of 6 hours at a temperature of 30° C., and after the entire amount had been added the mixture was agitated further for 20 hours at the same temperature to cause reaction.

After the reaction had completed, 16% aqueous sodium hydroxide solution was added to the reacted mixed solution to neutralize the solution, after which 250 g of toluene was added. The obtained mixed solution was heated to 60° C., and then the water layer was separated and the oil layer containing the target product was obtained. Next, 100 g of water was added to the obtained oil layer, the mixture was heated to 60° C., and the water layer was separated. The obtained oil layer was condensed at normal pressure, and 160 g of cyclohexane was added to the obtained concentrate at a temperature of 80° C. to cause crystallization. After cooling, the obtained crystal was filtered to obtain 103.4 g of coarse crystal containing the solvent. This coarse crystal was again introduced into a 1-liter four-way flask and dissolved by adding 247 g of toluene. The obtained solution was condensed at normal pressure and 150 g of cyclohexane was added to the concentrate to cause crystallization.

The crystallization liquid was cooled and the precipitated crystal was filtered and dried to obtain 67.3 g of the target product, or 2,6-bis-[(3-formyl-4-hydroxyphenyl)methyl]-4-cyclohexylphenol, as a white to yellowish powder crystal with a purity of 93.4% (measured by high-speed liquid chromatography).

The yield with respect to 2,6-di(hydroxymethyl)-4-cyclohexylphenol was 49.0%.

Mass spectrometry LC-MS (APCI$^-$)

Analysis result: Molecular weight 446 (M-H)$^-$

Melting point (differential thermal analysis): 142.3° C.

Proton nuclear magnetic resonance spectrum (400 Mz, solvent: DMSO-d6)

TABLE 2

| ppm | Assignment | Signal pattern | Number of protons |
|---|---|---|---|
| 10.52 | —CHO | s | 2 |
| 10.22 | Ph—OH | s | 2 |
| 8.30 | Ph—OH | s | 1 |
| 7.49-6.78 | Ph—H | m | 8 |
| 3.86 | —CH$_2$ | s | 4 |
| 2.51-2.50 | —CH (cyclohexyl) | m | 1 |
| 1.70-1.16 | —CH$_2$ (cyclohexyl) | m | 10 |

Example 3

Synthesis of 1,1-bis-[3-(3-formyl-4-hydroxyphenyl) methyl-4-hydroxy-5-cyclohexylphenyl]cyclohexane (Compound a)

Into a nitrogen-substituted 1-liter four-way flask equipped with a reflux condenser, thermometer and agitator, 244.0 g (2.0 mol) of salicyl aldehyde was introduced and then 114.0 g (1.0 mol) of trifluoroacetic acid was drip-fed and mixed over a period of 30 minutes at room temperature. Into the mixed solution, 98.4 g (0.2 mol) of 1,1-bis-(3-cyclohexyl-4-hydroxy-5-hydroxymethylphenyl)cyclohexane was added intermittently over a period of 6 hours at a temperature of 30° C., after which the mixture was agitated continuously for 18 hours at 30° C. After the reaction had completed, 210 g of toluene was added and 16% aqueous sodium hydroxide solution was then added to neutralize the mixture. The neutralized liquid was heated to 70° C., and the bottom water layer was removed by means of separation. Next, ion exchanged water was added to the oil layer and the mixture was agitated further at 70° C., after which the water layer was separated. The obtained oil layer was decompressed and distilled and then heated at 2.7 kPa to 160° C. to condense the liquid. The residue was mixed with 140 g of toluene at 110° C., after which 280 g of cyclohexane was added at 80° C. to cause crystallization. Crystal was filtered from the crystallization liquid to obtain 108.9 g of the target product (the yield was 77.8% with respect to hydroxymethyl compound).

Mass spectrometry LC-MS (APCI⁻)
Analysis result: Molecular weight 700 (M-H)⁻
Proton nuclear magnetic resonance spectrum (400 MHz, solvent: DMSO-d6)
[Chemical Formula 51]

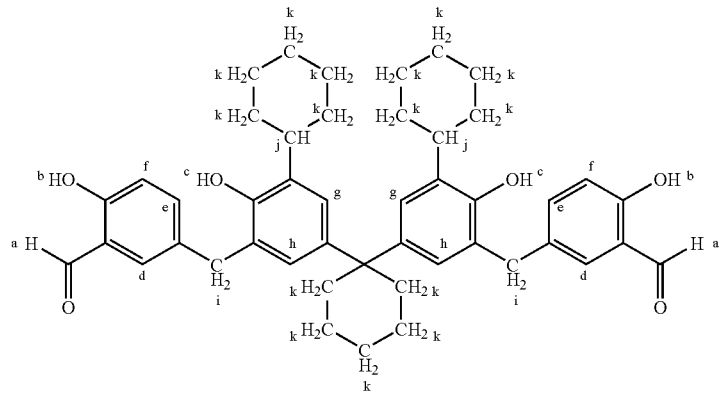

TABLE 3

| ppm | Assignment | Signal pattern | Number of protons |
|---|---|---|---|
| 10.49 | a | s | 2 |
| 10.19 | b | s | 2 |
| 7.98 | c | s | 2 |
| 7.49 | d | d | 2 |
| 7.27 | e | dd | 2 |
| 6.85 | f | d | 2 |
| 6.81 | g | s | 2 |
| 6.77 | h | s | 2 |
| 3.80 | i | s | 4 |
| 2.88-2.82 | j | m | 2 |
| 2.09-1.14 | k | m | 30 |

<Synthesis of Polynuclear Polyphenol Compound>

Example 4

Synthesis of 2,6-bis-{[3-di(4-hydroxy-2,5-dimethylphenyl)methyl-4-hydroxyphenyl]methyl}-4-methylphenol (Compound A)

Into a 3-liter four-way flask equipped with a thermometer and agitator, 305 g (2.5 mol) of 2,5-xylenol and 437.3 g (1.68 times by weight relative to 2,5-xylenol) of methanol were introduced and dissolved under agitation at a temperature of 30° C. After dissolution, 103.7 g (2.84 mol) of hydrochloric acid gas was blown into the mixture at a temperature of 30° C., after which 188.0 g (0.5 mol) of the 2,6-bis-[(3-formyl-4-hydroxyphenyl)methyl]-4-methylphenol powder synthesized in Example 1 was added intermittently over a period of 1 hour at a temperature of 30° C. to cause reaction. The mixture was reacted further under agitation for 5 hours at the same temperature. After the reaction had completed, 16% aqueous sodium hydroxide solution was drip-fed into the obtained reaction liquid to neutralize the liquid. Crystal precipitated during the neutralization, and the temperature at the end of neutralization was 63° C. After the neutralization, the reacted mixture was cooled to 32° C. and the precipitated crystal was filtered to obtain 829.3 g of coarse crystal containing the solvent.

This coarse crystal was introduced again into a 3-liter four-way flask, and 1268.1 g of methyl isobutyl ketone and 400 g of water were added and the mixture was agitated for 30 minutes at a temperature of 70° C. to dissolve the crystal, after which the water layer was separated to remove the inorganic salt. The obtained oil layer was washed with water again, the water layer was separated, and the obtained oil layer was condensed at normal pressure, after which 843.2 g of toluene was added to the resulting concentrate and the concentrate was cooled to cause crystallization. The precipitated crystal was filtered and dried to obtain 381.0 g of the target product as a yellowish powder crystal with a purity of 97.6% (measured by high-speed liquid chromatography) and melting point of 275.8° C. (measured by differential thermal analysis). (The yield with respect to the material 2,6-bis-[(3-formyl-4-hydroxyphenyl)methyl]-4-methylphenol was 93.1%.)

Mass spectrometry LC-MS (APCI⁻)
Analysis result: Molecular weight 828 (M-H)⁻
Proton nuclear magnetic resonance spectrum (400 Mz, solvent: DMSO-d6)

TABLE 4

| Shift | Number of protons | Signal | Assignment |
|---|---|---|---|
| 2.0~2.1 | 27 | m | Ø-CH3 |
| 3.7 | 4 | m | >CH2 |
| 5.7 | 2 | s | >CH— |
| 6.4~6.8 | 16 | m | Ø-H |
| 7.9 | 1 | s | Ø-OH |
| 8.8 | 4 | s | Ø-OH |
| 9.0 | 2 | s | Ø-OH |

[Chemical Formula 52]

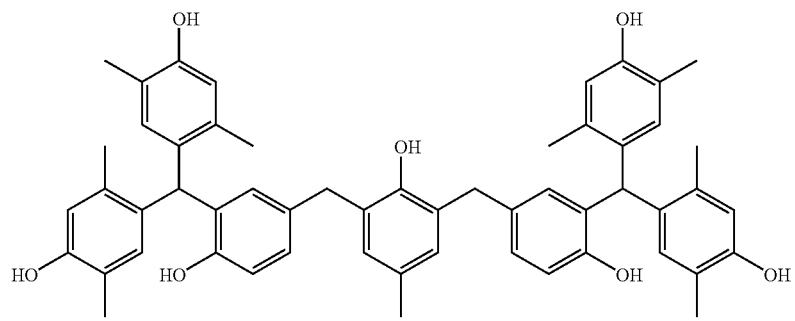

(Compound 6)

Example 5

Synthesis of 2,6-bis-{[3,5-di(5-cyclohexyl-4-hydroxy-2-methylphenyl)methyl-4-hydroxyphenyl]methyl}-4-methylphenol (Compound G)

Into a 3-liter four-way flask equipped with a thermometer and agitator, 376.2 g (1.98 mol) of 3-methyl-6-cyclohexyl phenol and 92.8 g of methanol were introduced and dissolved under agitation at a temperature of 30° C. After dissolution, 58.4 g of hydrochloric acid gas was blown into the mixture at a temperature of 30° C., after which 338.4 g of methanol was added and then 169.2 g (0.45 mol) of the 2,6-bis-[(3-formyl-4-hydroxyphenyl)methyl]-4-methylphenol synthesized in Example 1 was added over a period of 1 hour 30 minutes at a temperature of 40° C. to cause reaction. When the mixture was reacted further under agitation at the same temperature, crystal precipitated after 1 hour. The reaction was continued further for 1 hour. After the reaction had completed, 16% aqueous sodium hydroxide solution was drip-fed into the obtained reaction liquid to neutralize the liquid. Thereafter, the reacted mixture was heated to 60° C., 500 g of toluene and 500 g of cyclohexane were added, and the mixture was cooled to 25° C. The precipitated crystal was filtered to obtain 430 g of coarse crystal containing the solvent.

This coarse crystal was introduced again into a 3-liter four-way flask, and 975 g of propyl acetate and 400 g of water were added and the mixture was heated to a temperature of 70° C. to dissolve the crystal, after which the water layer was separated to obtain the oil layer containing the target product. The obtained oil layer was washed with water and condensed at normal pressure, after which 800 g of toluene was added to the resulting concentrate and the concentrate was cooled to cause crystallization. The precipitated crystal was filtered and dried to obtain 373.9 g of the target product as a yellowish powder crystal with a purity of 97.9% (measured by high-speed liquid chromatography) and melting point of 271.8° C. (measured by differential thermal analysis). (The yield with respect to the material 2,6-bis-[(3-formyl-4-hydroxyphenyl)methyl]-4-methylphenol was 75.5%.)

Mass spectrometry LC-MS (APCI⁻)

Analysis result: Molecular weight 1100 (M-H)⁻

Proton nuclear magnetic resonance spectrum (400 Mz, solvent: DMSO-d6)

TABLE 5

| Shift (ppm) | Number of protons | Signal | Assignment |
| --- | --- | --- | --- |
| 1.05-1.65 | 40 | m | —CH$_2$ (cyclohexyl) |
| 2.04-2.08 | 15 | m | —CH$_3$ |
| 2.68-2.71 | 4 | t | —CH (cyclohexyl) |
| 3.67 | 4 | s | —CH$_2$ |
| 5.76 | 2 | s | —CH |
| 6.49-6.85 | 16 | m | Ph—H |
| 7.85 | 1 | s | —OH (Ph—OH): ③ |
| 8.78 | 4 | s | —OH (Ph—OH): ② |
| 8.99 | 2 | s | —OH (Ph—OH): ① |

[Chemical Formula 53]

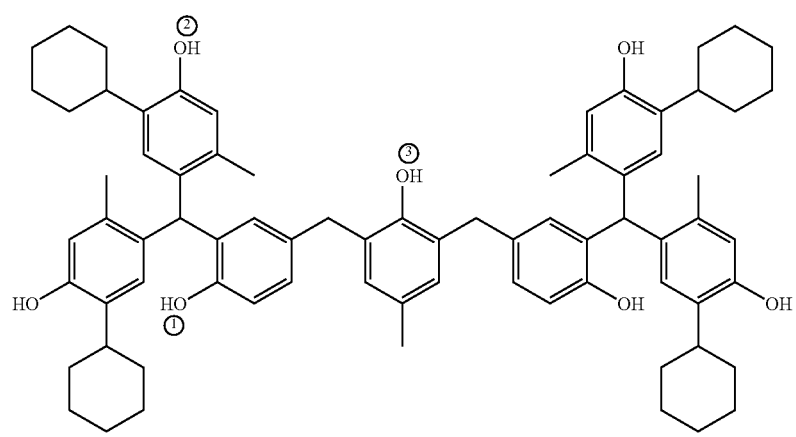

(Compound 7)

Example 6

Synthesis of 1,1-bis-{3-(3-[bis-(4-hydroxy-2,5-dimethylphenyl)methyl]-4-hydroxyphenyl)methyl-4-hydroxy-5-cyclohexylphenyl}cyclohexane (Compound H)

Into a 500-mL four-way flask, 33.6 g (0.28 mol) of 2,5-xylenol, 50.4 g of methanol and 10.1 g of 35% aqueous hydrochloric acid solution were introduced, after which 38.5 g (0.06 mol) of the compound obtained in Example 3 was added intermittently over a period of 2 hours at 40° C. to cause reaction. Thereafter, the mixture was agitated further for 46 hours at 40° C.

After the reaction had completed, 16% aqueous sodium hydroxide solution was added to neutralize the reaction liquid, after which the liquid was heated to 60° C., and then 102.4 g of methyl isobutyl ketone was added to dissolve the solid content and the water layer was separated and removed. Thereafter, 180 g of solvent was removed via distillation, and 127 g of toluene and 32 g of cyclohexane were added to obtain coarse crystal through the crystallization, cooling and filtering processes. The obtained coarse crystal was dissolved by adding 100 g of propyl acetate and 60 g of water and heating the mixture to 70° C., and the water layer was separated and removed. Thereafter, the oil layer was condensed and 94 g of solvent was removed, after which toluene and cyclohexane were added to obtain, through the crystallization, cooling, filtering and drying processes, 43.4 g of yellowish powder crystal (purity of crystal 97.4% (measured by high-speed liquid chromatography), melting point 178.5° C. (DSC peak-top), yield 68.5% (with respect to aldehyde)).

Mass spectrometry LC-MS (APCI⁻)

Analysis result: Molecular weight 1153 (M-H)⁻

Proton nuclear magnetic resonance spectrum (400 MHz, solvent: DMSO-d6)

[Chemical Formula 54]

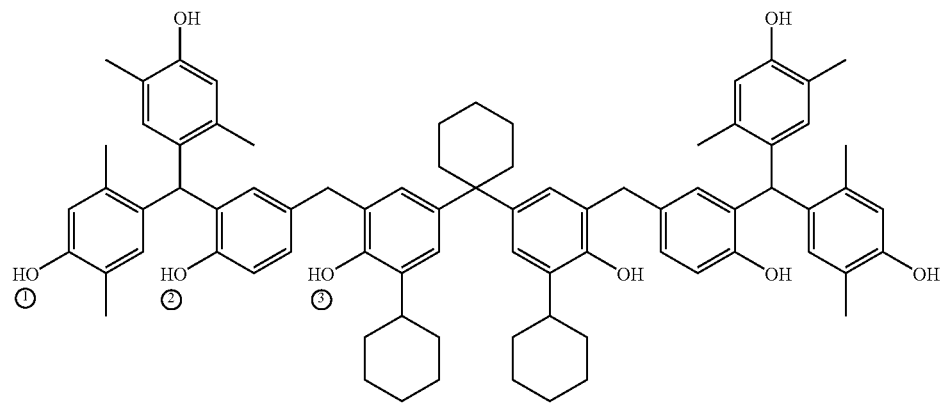

TABLE 6

| Shift (ppm) | Number of protons | Signal | Assignment |
|---|---|---|---|
| 1.18-1.72 | 26 | m | —CH$_2$ (cyclohexyl) |
| 1.93-1.96 | 24 + 4 | m | —CH$_3$ + —CH$_2$ (cyclohexyl) |
| 2.85 | 2 | t | —CH (cyclohexyl) |
| 3.63 | 4 | s | —CH$_2$ |
| 5.65 | 2 | s | —CH |

TABLE 6-continued

| Shift (ppm) | Number of protons | Signal | Assignment |
|---|---|---|---|
| 6.54-6.74 | 18 | m | Ph—H |
| 7.76 | 2 | s | —OH (Ph—OH): ③ |
| 8.84 | 4 | s | —OH (Ph—OH): ① |
| 8.96 | 2 | s | —OH (Ph—OH): ② |

Example 7

Synthesis of 1,1-bis-{3-(3-[bis-(5-cyclohexyl-4-hydroxy-2-methylphenyl)methyl]-4-hydroxyphenyl)methyl-4-hydroxy-5-cyclohexylphenyl}cyclohexane (Compound N)

Into a nitrogen-substituted 200-mL four-way flask equipped with a reflux condenser, thermometer and agitator, 4.8 g (0.025 mol) of 5-methyl-2-cyclohexyl phenol and 1.2 g of methanol were introduced, after which 1.7 g of hydrochloric acid gas was blown into the mixture at 30° C. Thereafter, 7.1 g of methanol was added, and then 3.5 g (5.0 mmol) of the compound obtained in Example 3 was added under agitation over a period of 1 hour to cause reaction. Thereafter, the mixture was agitated further for 2 hours at 40° C.

After the reaction had completed, 11.7 g of 16% aqueous sodium hydroxide solution was added to neutralize the reaction liquid (crystal precipitated during the neutralization), after which the liquid was heated to 55° C. and 14.7 g of toluene was added to dissolve the solid content, and the water layer was separated and removed. Thereafter, 1.0 g of methyl isobutyl ketone and 7.0 g of water were added to the obtained oil layer and the mixture was agitated and heated to 70° C., after which the water layer was separated and removed and 3.5 g of cyclohexane and 21 g of toluene were added to the oil layer to cause crystallization. The resulting mixture was cooled to 25° C. and filtered to obtain 11.5 g of coarse crystal. The obtained coarse crystal, 14.2 g of propyl acetate and 7.0 g of water were introduced into a 200-mL four-way flask, and the mixture was heated to 70° C. to dissolve the crystal, after which the flask was left stationary and the water layer was removed. The obtained oil layer was mixed with 60 g of water and the same operation was repeated to wash the oil layer with water and separate the oil layer. Next, the obtained oil layer was condensed at normal pressure and 9.8 g of solvent was removed, after which 14 g of cyclohexane was added to precipitate crystal. The resulting mixture was cooled to 25° C., filtered, and dried, to obtain 4.7 g of the target product as a yellowish powder (purity 98.5% (measured by high-speed liquid chromatography), melting point 176.8° C. (differential thermal analysis, peaktop), yield 81.5% (with respect to the material aldehyde)).

Mass spectrometry LC-MS (APCI⁻)
Analysis result: Molecular weight 1425 (M-H)⁻
Proton nuclear magnetic resonance spectrum (400 MHz, solvent: DMSO-d6)
[Chemical Formula 55]

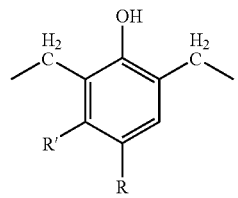

General formula (2)

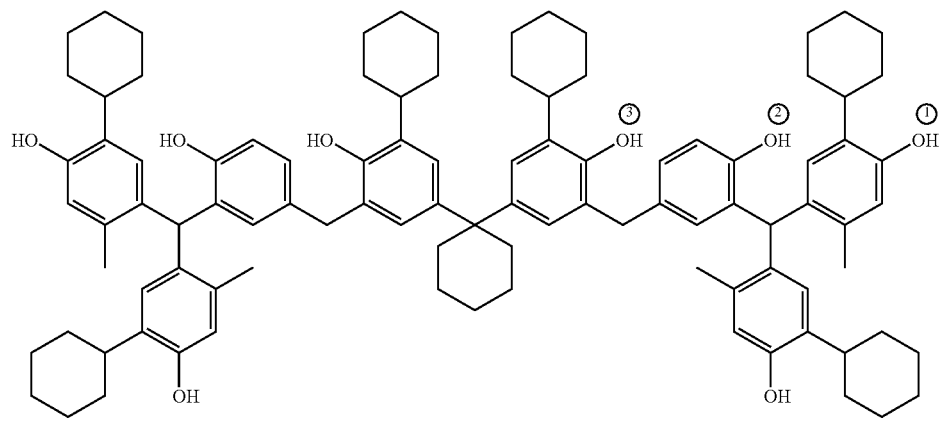

TABLE 7

| Shift (ppm) | Number of protons | Signal | Assignment |
| --- | --- | --- | --- |
| 1.08-1.99 | 82 | m | —CH₃ + —CH₂ (cyclohexyl) |
| 2.21 | 4 | t | —CH (cyclohexyl) |
| 2.36 | 2 | t | —CH (cyclohexyl) |
| 3.14 | 4 | s | —CH₂ |
| 5.22 | 2 | s | —CH |
| 6.03-6.21 | 18 | m | Ph—H |
| 7.17 | 2 | s | —OH (Ph—OH): ③ |
| 8.26 | 4 | s | —OH (Ph—OH): ① |
| 8.43 | 2 | s | —OH (Ph—OH): ② |

What is claimed is:

1. A bis-(hydroxybenzaldehyde) compound expressed by

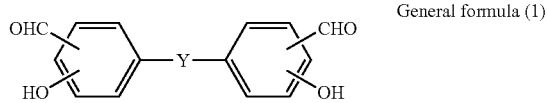

General formula (1)

wherein Y represents a bivalent group having a methylene group at both ends, as expressed by general formula (2) or general formula (3) given below, wherein R represents an alkyl group with 1 to 4 carbon atoms or cycloalkyl group with 5 or 6 carbon atoms, while R' represents a hydrogen atom or methyl group,

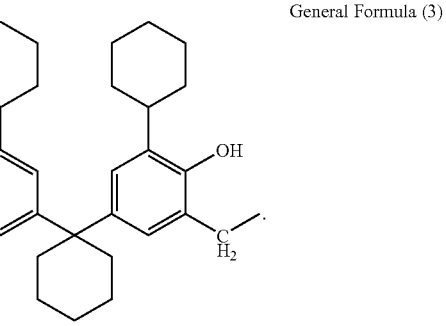

General Formula (3)

2. A bis-(hydroxybenzaldehyde) compound according to claim 1, which is expressed by

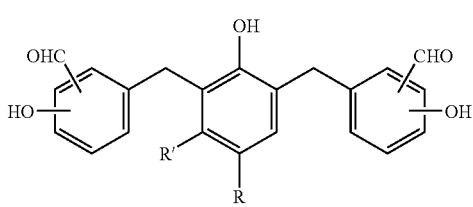

General formula (4)

wherein R and R' represent the corresponding items in general formula (2), respectively.

3. A bis-(hydroxybenzaldehyde) compound according to claim 1, which is expressed by General formula (5)

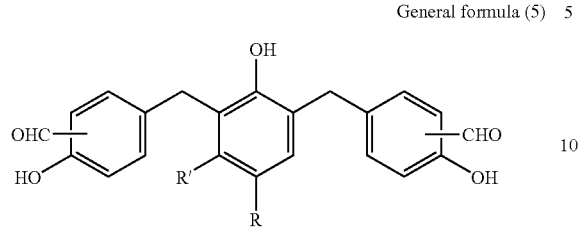

wherein R and R' represent the corresponding items in general formula (2), respectively.

4. A bis-(hydroxybenzaldehyde) compound according to claim 1, which is expressed by general formula (7) given below General formula (7)

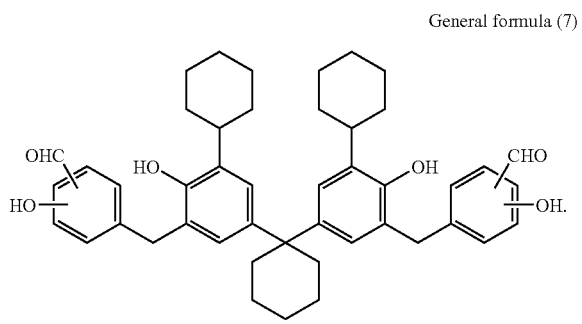

5. 1,1-bis-[3-(3-formyl-4-hydroxyphenyl)methyl-4-hydroxy-5-cyclohexyl phenyl]cyclohexane.

6. A polynuclear polyphenol compound expressed by

General formula (8)

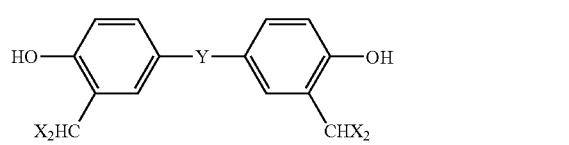

wherein Y represents a bivalent group having a methylene group at both ends, as expressed by general formula (2) or general formula (3) given below, General formula (2)

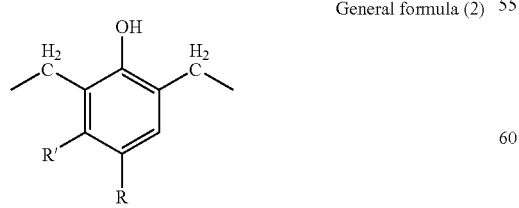

wherein R represents an alkyl group with 1 to 4 carbon atoms or cycloalkyl group with 5 or 6 carbon atoms, while R' represents a hydrogen atom or methyl group, General Formula (3)

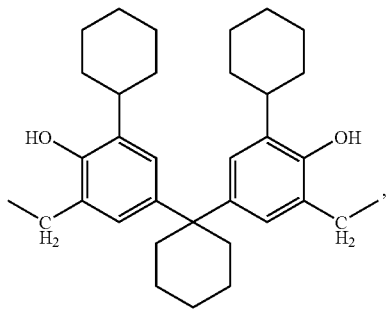

while X represents a hydroxyphenyl group that may be substituted by an alkyl group expressed by general formula (9) given below, General formula (9)

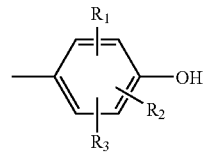

wherein $R_1$, $R_2$, and $R_3$ each represent an independent hydrogen atom, alkyl group with 1 to 4 carbon atoms, or cycloalkyl group with 5 or 6 carbon atoms.

7. A polynuclear polyphenol compound according to claim 6, which is expressed by general formula (10) given below General formula (10)

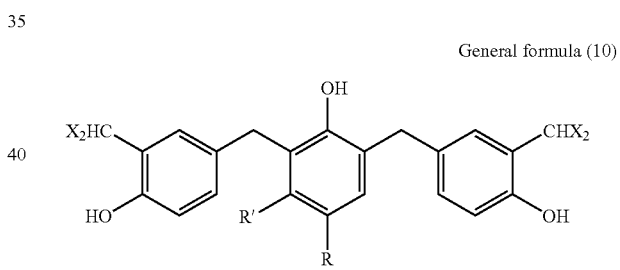

wherein R and R' represent the corresponding items in general formula (2), respectively, while X is the same as the hydroxyphenyl group in general formula (9).

8. A polynuclear polyphenol compound according to claim 6, which is expressed by general formula (11) given below General formula (11)

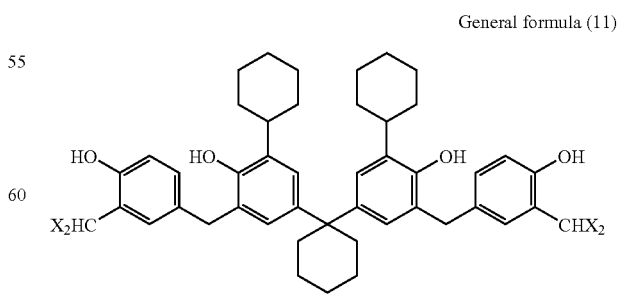

wherein X represents the corresponding item in general formula (9).

9. A method for producing a bis-(hydroxybenzaldehyde) compound according to claim 1, characterized by reacting in the presence of trihalogenated acetic acid catalyst or phosphoric acid catalyst a 2,6-di(hydroxymethyl)-4-alkyl phenol expressed by general formula (12), with a hydroxybenzaldehyde expressed by general formula (14)

General formula (12)
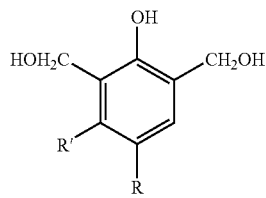

wherein R and R' represent the corresponding items in general formula (2), respectively, General formula (14)
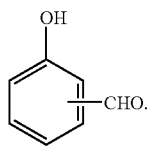

10. A method for producing a bis-(hydroxybenzaldehyde) according to claim 1, characterized by reacting in the presence of trihalogenated acetic acid catalyst a 1,1-bis-(3-cyclohexyl-4-hydroxy-5-hydroxymethyl phenyl)cyclohexane expressed by general formula (13), with a hydroxybenzaldehyde expressed by general formula (14)

General formula (13)
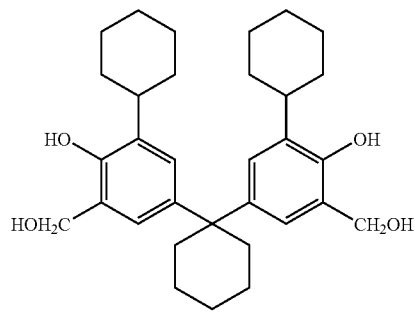

General formula (14)
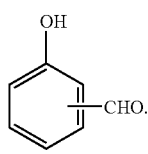

11. A bis-(hydroxybenzaldehyde) compound according to claim 2, which is expressed by General formula (5)
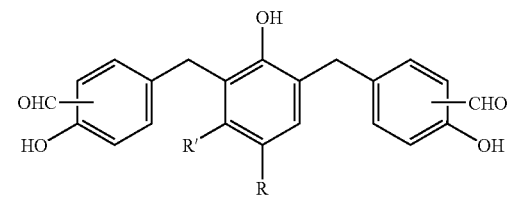

wherein R and R' represent the corresponding items in general formula (2), respectively.

12. A method for producing a bis-(hydroxybenzaldehyde) compound according claim 2, characterized by reacting in the presence of trihalogenated acetic acid catalyst or phosphoric acid catalyst a 2,6-di(hydroxymethyl)-4-alkyl phenol expressed by general formula (12), with a hydroxybenzaldehyde expressed by general formula (14)

General formula (12)
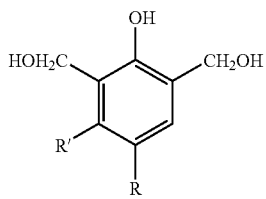

wherein R and R' represent the corresponding items in general formula (2), respectively, General formula (14)

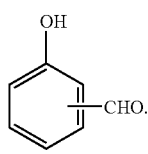

13. A method for producing a bis-(hydroxybenzaldehyde) compound according claim 3, characterized by reacting in the presence of trihalogenated acetic acid catalyst or phosphoric acid catalyst a 2,6-di(hydroxymethyl)-4-alkyl phenol expressed by general formula (12), with a hydroxybenzaldehyde expressed by general formula (14)

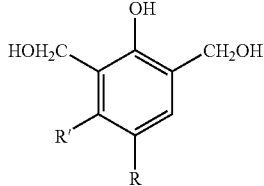

General formula (12)

wherein R and R' represent the corresponding items in general formula (2), respectively,

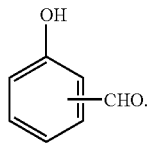

General formula (14)

14. A method for producing a bis-(hydroxybenzaldehyde) according to claim 4, characterized by reacting in the presence of trihalogenated acetic acid catalyst a 1,1-bis-(3-cyclohexyl-4-hydroxy-5-hydroxymethyl phenyl)cyclohexane expressed by general formula (13), with a hydroxybenzaldehyde expressed by general formula (14)

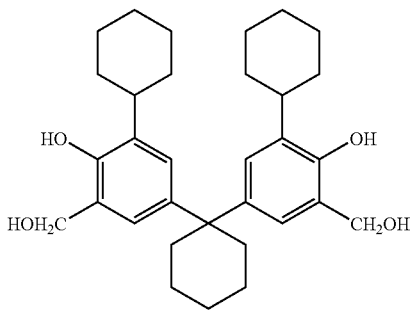

General formula (13)

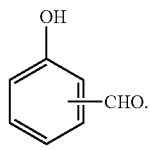

General formula (14)

15. A method according to claim 9, wherein an amount of the hydroxybenzaldehyde used per 1 mol of the 2,6-di(hydroxymethyl)-4-alkyl phenol is in a range of 2.1 to 10 mol.

16. A method according to claim 9, wherein an amount of the acid catalyst used per 1 mol of the hydroxybenzaldehyde is in a range of 0.1 to 10 mol.

17. A method according to claim 9, wherein reaction temperature is in a range of 0 to 80° C.

* * * * *